United States Patent
Tominaga et al.

(10) Patent No.: US 11,464,436 B2
(45) Date of Patent: Oct. 11, 2022

(54) AWAKENING DEGREE DETERMINATION APPARATUS AND AWAKENING DEGREE DETERMINATION METHOD

(71) Applicant: Mitsubishi Electric Corporation, Chiyoda-ku (JP)

(72) Inventors: Kenta Tominaga, Tokyo (JP); Hiroaki Kitano, Tokyo (JP)

(73) Assignee: MITSUBISHI ELECTRIC CORPORATION, Tokyo (JP)

(*) Notice: Subject to any disclaimer, the term of this patent is extended or adjusted under 35 U.S.C. 154(b) by 244 days.

(21) Appl. No.: 16/620,342

(22) PCT Filed: Sep. 22, 2017

(86) PCT No.: PCT/JP2017/034293
§ 371 (c)(1),
(2) Date: Dec. 6, 2019

(87) PCT Pub. No.: WO2019/058503
PCT Pub. Date: Mar. 28, 2019

(65) Prior Publication Data
US 2020/0205715 A1    Jul. 2, 2020

(51) Int. Cl.
*B60T 7/14* (2006.01)
*A61B 5/18* (2006.01)
*B62D 15/02* (2006.01)

(52) U.S. Cl.
CPC .............. *A61B 5/18* (2013.01); *B62D 15/021* (2013.01)

(58) Field of Classification Search
CPC .... A61B 5/18; B60K 28/066; B60K 31/0066; B60T 2201/086; B60W 2040/0818; B60W 40/09; G08B 21/0407; G08B 21/06
(Continued)

(56) References Cited

U.S. PATENT DOCUMENTS

| 4,463,347 A | 7/1984 | Seko et al. |
| 6,393,361 B1 | 5/2002 | Yano et al. |

(Continued)

FOREIGN PATENT DOCUMENTS

| DE | 102004022581 A1 | 4/2005 |
| DE | 102006051930 A1 | 5/2008 |

(Continued)

OTHER PUBLICATIONS

Office Action dated Jul. 30, 2020, in corresponding German Application No. 11 2017 007 868.7, 13 pages.
(Continued)

*Primary Examiner* — Naomi J Small
(74) *Attorney, Agent, or Firm* — Xsensus LLP

(57) ABSTRACT

An object is to provide a technique capable of accurately determining an awakening degree. An awakening degree determination apparatus includes a change amount acquisition unit, a frequency calculation unit, and an awakening degree determination unit. The change amount acquisition unit acquires an angle change amount, an inclination change amount, and a position change amount. The frequency calculation unit calculates an angle frequency, an inclination frequency, and a position frequency. When at least one of the angle frequency, the inclination frequency, and the position frequency exceeds a fourth threshold value, a fifth threshold value, and a sixth threshold value, the awakening degree determination unit determines that an awakening degree of a driver of the vehicle decreases.

10 Claims, 20 Drawing Sheets

(58) Field of Classification Search
USPC .......................................................... 340/438
See application file for complete search history.

(56) References Cited

U.S. PATENT DOCUMENTS

| | | | | |
|---|---|---|---|---|
| 2009/0021356 | A1* | 1/2009 | Galley | B60K 28/066 |
| | | | | 701/41 |
| 2009/0322506 | A1 | 12/2009 | Schmitz | |
| 2010/0102972 | A1* | 4/2010 | Middlekauff | B62D 15/0215 |
| | | | | 340/576 |
| 2015/0092056 | A1* | 4/2015 | Rau | B60R 11/04 |
| | | | | 348/148 |
| 2017/0349186 | A1* | 12/2017 | Miller | B60W 50/0098 |
| 2018/0299890 | A1* | 10/2018 | Ewert | G05D 1/0088 |

FOREIGN PATENT DOCUMENTS

| | | |
|---|---|---|
| DE | 102008007149 A1 | 10/2008 |
| DE | 102011013663 A1 | 9/2012 |
| DE | 102008007149 B4 | 5/2019 |
| JP | 57-66026 A | 4/1982 |
| JP | 7-9880 A | 1/1995 |
| JP | 11-339200 A | 12/1999 |
| JP | 2000-326757 A | 11/2000 |
| JP | 2008-250859 A | 10/2008 |
| JP | 2013-140605 A | 7/2013 |
| JP | 2017-107299 A | 6/2017 |

OTHER PUBLICATIONS

International Search Report dated Nov. 7, 2017 in PCT/JP2017/034293 filed Sep. 22, 2017.
Notice of Reasons for Refusal dated Jan. 30, 2018 in Japanese Patent Application No. 2017-565877 (with unedited computer generated English translation), citing documents AO-AS therein, 8 Pages.
German Office Action dated Jul. 22, 2022, in corresponding German Application No. 11 2017 007 868.7.

* cited by examiner

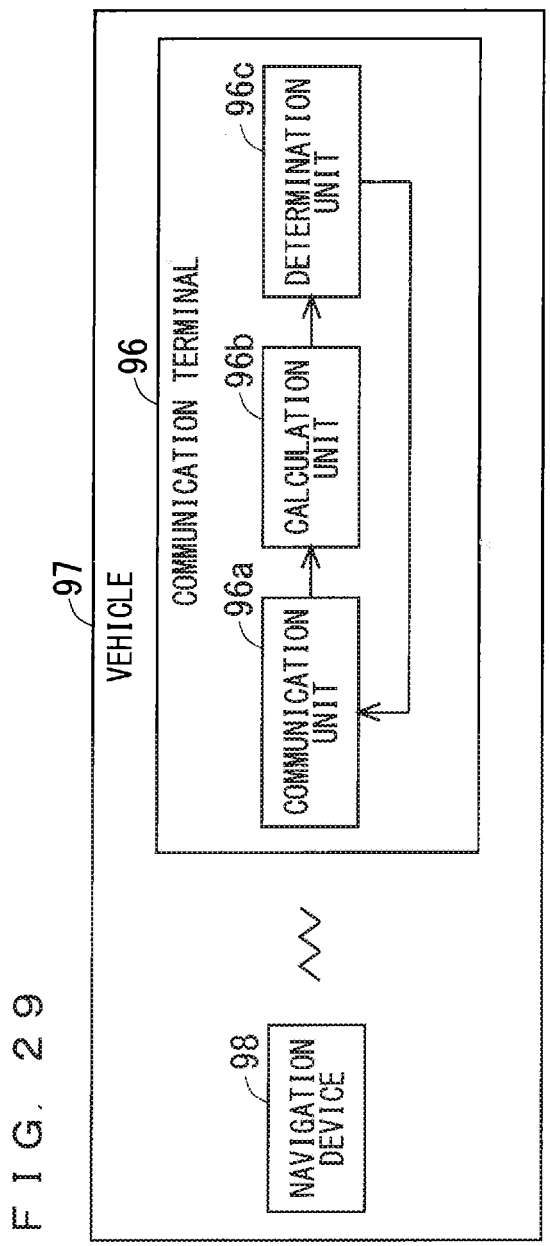

AWAKENING DEGREE DETERMINATION APPARATUS AND AWAKENING DEGREE DETERMINATION METHOD

TECHNICAL FIELD

The present invention relates to an awakening degree determination apparatus and an awakening degree determination method.

BACKGROUND ART

Reduction in an awakening degree due to drowsiness of a driver while driving causes deviation from a traffic lane or an accident such as a collision with a vehicle ahead. Thus, developed are a device determining an awakening degree and a device transmitting a warning when the awakening degree decreases. A conventional awakening degree determination apparatus determines an awakening degree based on steering information. For example, Patent Document 1 evaluates four points of (1) a frequency of a minimal value of time before a vehicle goes over a traffic lane, (2) a frequency of no change of steering angle for a predetermined period of time, (3) a frequency of occurrence of a corrected steering after the steering angle does not change for the predetermined period of time, and (4) a frequency of no change of steering angle while a lateral position which is a position of a vehicle in a lane width direction exceeds a threshold value. When at least two of the frequencies described in (1), (2), and (3) exceed each predetermined boundary value or when both frequencies described in (1) and (4) exceed each predetermined boundary value, the occurrence of the reduction in the awakening degree is determined (for example, Patent Document 1).

PRIOR ART DOCUMENTS

Patent Documents

Patent Document 1: Japanese Patent Application Laid-Open No. 2013-140605

SUMMARY

Problem to be Solved by the Invention

Such an awakening degree determination apparatus has a problem that variety of a drive pattern in the reduction in the awakening degree of a driver cannot be considered. That is to say, in a drive pattern in a drowsy state where a pulsing corrected steering does not occur but a long-period wobble (meandering) occurs, a difference does not occur in a fluctuation of a steering cycle and a fluctuation of amplitude. The technique in Patent Document 1 cannot appropriately determine the awakening degree on such a drive pattern.

The details are as follows. Firstly, with respect to (1) the frequency of a minimal value of time before a vehicle goes over a traffic lane, even in a state where the awakening degree does not decrease, that is to say, even when the driver is in an awake state, the meandering occurs slightly but constantly in the vehicle, thus a time before the vehicle goes over the traffic lane changes. Thus, when a meandering cycle changes to the same degree as that in the awake state and only the amplitude changes even in a state where the driver is in a drowsy state, there is no change in the frequency of the minimal value of time before the vehicle goes over the traffic lane. Next, with respect to (2) the frequency of no change of steering angle for a predetermined period of time, (3) the frequency of occurrence of a corrected steering after the steering angle does not change for the predetermined period of time, and (4) the frequency of no change of steering angle while a lateral position of a vehicle exceeds a threshold value, the meandering occurs when the steering angle is not appropriate for a shape of the lane, so that presence or absence of the reduction in the awakening degree cannot be directly argued in accordance with presence or absence of the change of the steering angle, corrected steering, and meandering. Accordingly, the technique in Patent Document 1 cannot detect the drive pattern in the drowsy state where the meandering occurs without the occurrence of the pulsing corrected steering.

The present invention therefore has been made to solve the above problems, and it is an object of the present invention to provide a technique capable of accurately determining an awakening degree.

Means to Solve the Problem

An awakening degree determination apparatus according, to the present invention includes: a change amount acquisition unit acquiring an angle change amount which is a change amount of a steering angle of a vehicle in a first period which is predetermined, an inclination change amount which is a change amount of an inclination of a front and rear side of the vehicle with respect to a travel traffic lane of the vehicle in a second period which is, predetermined, and a position change amount which is a change amount of a lateral position of the vehicle in the travel traffic lane in a third period which is predetermined; a frequency calculation unit calculating an angle frequency which is a frequency in which the angle change amount exceeds a first threshold value which is predetermined, an inclination frequency which is a frequency in which the inclination change amount exceeds a second threshold value which is predetermined, and a position frequency which is a frequency in which the position change amount exceeds a third threshold value which is predetermined; and an awakening degree determination unit determining that an awakening degree of a driver of the vehicle decreases when at least one of the angle frequency, the inclination frequency, and the position frequency exceeds a fourth threshold value, a fifth threshold value, and a sixth threshold value which are predetermined on the angle frequency, the inclination frequency, and the position frequency, respectively.

Effects of the Invention

According to the present invention, when at least one of the angle frequency, the inclination frequency, and the position frequency exceeds the fourth threshold value, the fifth threshold value, and the sixth threshold value, it is determined that the awakening degree of the driver of the vehicle decreases. According to such a configuration, the awakening degree can be accurately determined.

These and other objects, features, aspects and advantages of the present invention will become more apparent from the following detailed description of the present invention when taken in conjunction with the accompanying drawings.

BRIEF DESCRIPTION OF DRAWINGS

FIG. 29 A block diagram illustrating a configuration of a communication terminal according to a modification example.

DESCRIPTION OF EMBODIMENT(S)

Embodiment 1

Described hereinafter is an example of a configuration that an awakening degree determination apparatus according to an embodiment 1 of the present invention is provided in a vehicle. In the description hereinafter, a vehicle provided with the awakening degree determination apparatus and subject to focus is referred to as "the subject vehicle".

Figure 1:
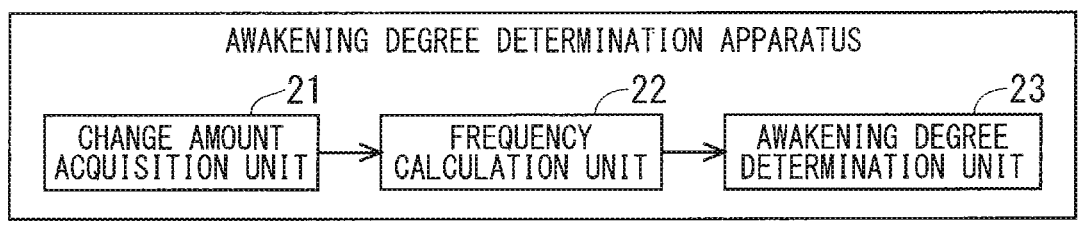
FIG. 1 A block diagram illustrating a schematic configuration of an awakening degree determination apparatus according to an embodiment 1.

FIG. 1 is a block diagram illustrating a schematic configuration of the awakening degree determination apparatus according to the present embodiment 1. The awakening degree determination apparatus illustrated in FIG. 1 includes a change amount acquisition unit 21, a frequency calculation unit 22, and an awakening degree determination unit 23.

The change amount acquisition unit 21 acquires an angle change amount, an inclination change amount, and a position change amount. The angle change amount is a change amount of a steering angle of the subject vehicle in a predetermined first period. The inclination change amount is a change amount of an inclination of a front and rear side of the subject vehicle with respect to a travel traffic lane of the subject vehicle in a predetermined second period. The travel traffic lane of the subject vehicle indicates a traffic lane along which the subject vehicle travels. The position change amount is a change amount of a lateral position of the subject vehicle in a travel traffic lane of the subject vehicle in a predetermined third period. The change amount acquisition unit 21 may acquire the angle change amount, which is calculated in a device located outside the awakening degree determination apparatus, from the device, or the change amount acquisition unit 21 itself may calculate and acquire the angle change amount. The same applies to the inclination change amount and the position change amount.

The frequency calculation unit 22 calculates an angle frequency, an inclination frequency, and a position frequency based on the angle change amount, the inclination change amount, and the position change amount acquired in the change amount acquisition unit 21. The angle frequency is a frequency in which the angle change amount exceeds a predetermined first threshold value. The inclination frequency is a frequency in which the inclination change amount exceeds a predetermined second threshold value.

The position frequency is a frequency in which the position change amount exceeds a predetermined third threshold value.

The awakening degree determination unit 23 determines that an awakening degree of a driver of the subject vehicle decreases when at least one of the angle frequency, the inclination frequency, and the position frequency calculated in the frequency calculation unit 22 exceeds a fourth threshold value, a fifth threshold value, and a sixth threshold value which are predetermined on the angle frequency, the inclination frequency, and the position frequency, respectively.

Outline of Embodiment 1

According to the awakening degree determination apparatus of the present embodiment 1 described above, when at least one of the angle frequency, the inclination frequency, and the position frequency exceeds the fourth threshold value, the fifth threshold value, and the sixth threshold value, it is determined that the awakening degree of the driver of the subject vehicle decreases. Such a configuration can appropriately meet a drive pattern in a drowsy state which differs widely between individuals, thus can accurately determine the awakening degree.

Embodiment 2

Figure 2:
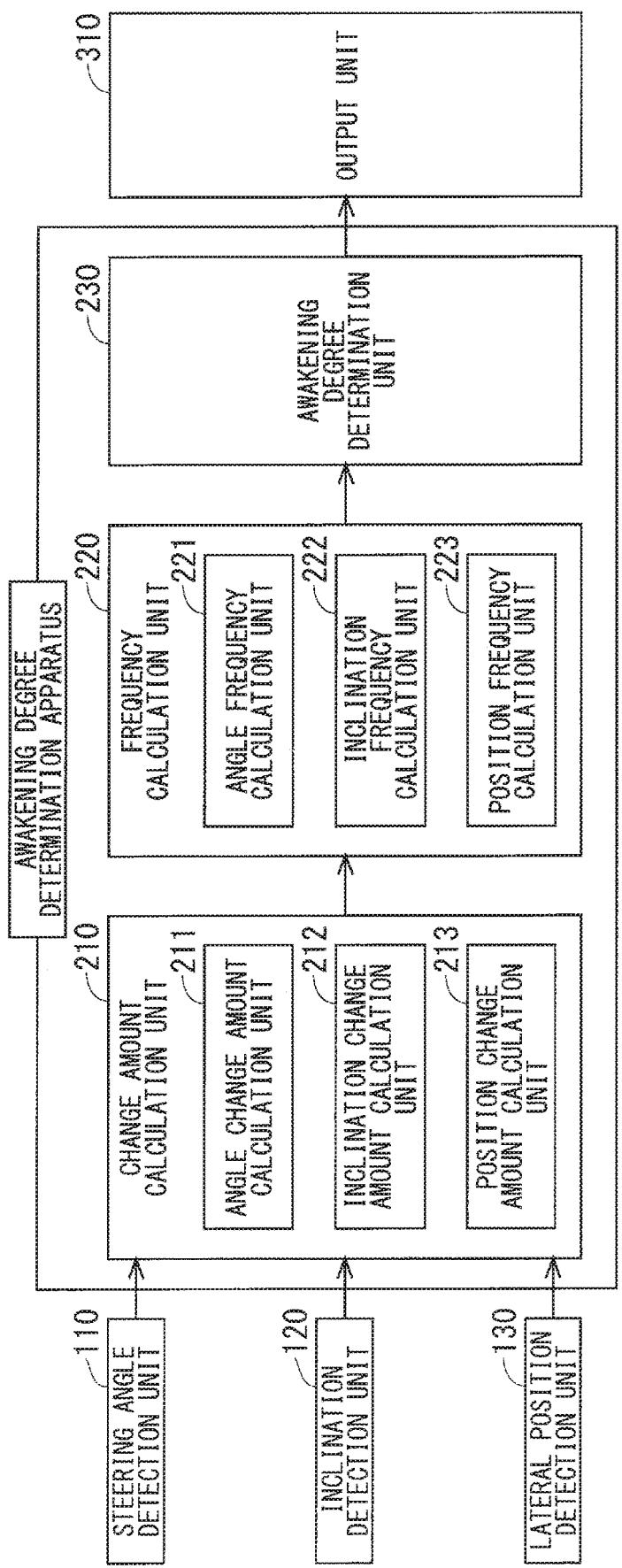
FIG. 2 A block diagram illustrating a schematic configuration of an awakening degree determination apparatus according to an embodiment 2.

FIG. 2 is a block diagram illustrating a schematic configuration of an awakening degree determination apparatus according to an embodiment 2 of the present invention.

A change amount calculation unit 210 illustrated in FIG. 2 corresponds to the change amount acquisition unit 21 illustrated in FIG. 1, and is a calculation unit calculating a change amount. The change amount calculation unit 210 internally includes an angle change amount calculation unit 311 calculating an angle change amount, an inclination change amount calculation unit 212 calculating an inclination change amount, and a position change amount calculation unit 213 calculating a position change amount.

A frequency calculation unit 220 illustrated in FIG. 2 corresponds to the frequency calculation unit 22 illustrated in FIG. 1, and is a calculation unit for calculating a frequency in which each change amount calculated in the change amount calculation unit 210 exceeds a corresponding threshold value. The frequency calculation unit 220 internally includes an angle frequency calculation unit 221 calculating an angle frequency, an inclination frequency calculation unit 222 calculating an inclination frequency, and a position frequency calculation unit 223 calculating a position frequency.

An awakening degree determination unit 230 illustrated in FIG. 2 corresponds to the awakening degree determination unit 23 illustrated in FIG. 1, and is a determination unit comparing each frequency calculated in the frequency calculation unit 220 with a corresponding threshold value and determining the awakening degree based on a comparison result thereof.

A steering angle detection unit 110, an inclination detection unit 120, and a lateral position detection unit 130 are connected, as input devices located outside the awakening degree determination apparatus, to the awakening degree determination apparatus.

The steering angle detection unit 110 is a detection unit for detecting a steering angle of the subject vehicle, and is a steering angle sensor mounted on an electrical power steering (EPS), for example.

The inclination detection unit 120 is a detection unit for detecting an inclination of a front and rear side of the subject vehicle with respect to a travel traffic lane of the subject vehicle, and is a white line recognition camera, for example. Alternatively, the inclination detection unit 120 may be, for example, map data and a satellite positioning system, or also may be map data and a LIDAR. The LIDAR indicates light detection and ranging or laser imaging detection and ranging.

The lateral position detection unit 130 is a detection unit for detecting a lateral position of the subject vehicle in a travel traffic lane of the subject vehicle, and is a white line recognition camera, for example. Alternatively, the lateral position detection unit 130 may be, for example, map data and a satellite positioning system, or also may be map data and a LIDAR.

An output unit 310 is connected, as an input device located outside the awakening degree determination apparatus, to the awakening degree determination apparatus. The output unit 310 is a device for attracting an attention of the driver of the subject vehicle or performing a safety precaution of the subject vehicle. The output unit 310 is a speaker sounding an alarm when the awakening degree determination unit 230 determines that the driver is in the drowsy state, for example. Alternatively, the output unit 310 is a display displaying a message for attracting an attention of the driver when the awakening degree determination unit 230 determines that the driver is in the drowsy state, for example. Alternatively, the output unit 310 is an advanced driver assistance system electronic control unit (ADAS-ECU) performing a safety precaution of automatically parking the vehicle by the side of a road when the awakening degree determination unit 230 determines that the driver is in the drowsy state, for example. Alternatively, the output unit 310 is an electrical power steering electronic control unit (EPS-ECU) vibrating a handle to promote the awakening of the driver when the awakening degree determination unit 230 determines that the driver is in the drowsy state, for example. Alternatively, the output unit 310 is an air conditioner fanning the driver to promote the awakening of the driver when the awakening degree determination unit 230 determines that the driver is in the drowsy state, for example.

Figure 3:
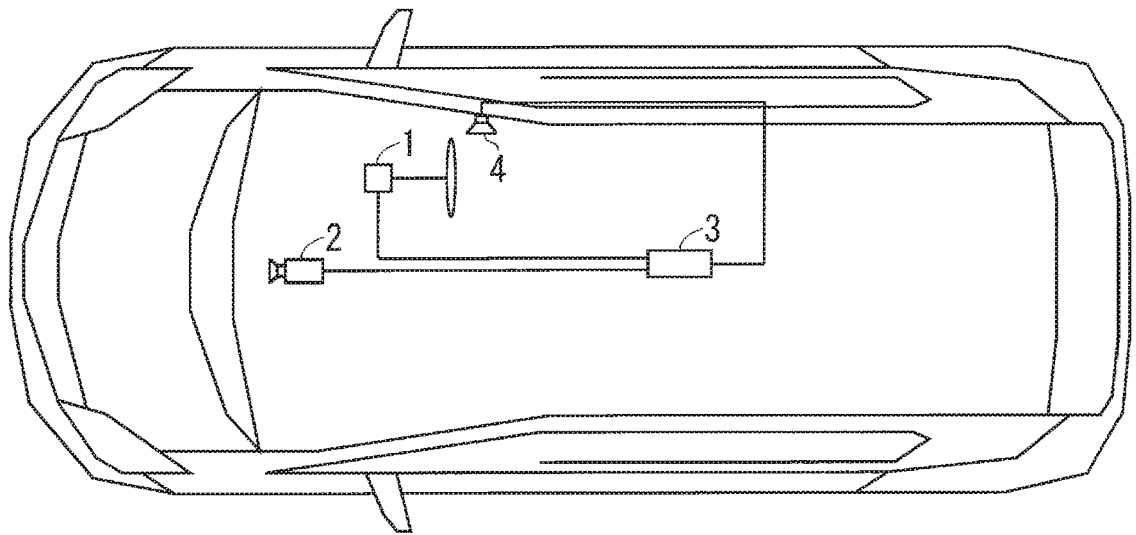
FIG. 3 A drawing illustrating a system configuration of the awakening degree determination apparatus according to the embodiment 2.

FIG. 3 is a drawing illustrating a system configuration of the awakening degree determination apparatus according to the present embodiment 2. The EPS-ECU 1, which is an ECU performing a control of an EPS, detects a steering angle and transmits the steering angle to an ADAS-ECU 3. A white line recognition camera 2, which is a camera for recognizing a white line, detects an inclination of a front and rear side of the subject vehicle with, respect to a travel traffic lane of the subject vehicle and a lateral position of the subject vehicle in the travel traffic lane of the subject vehicle and transmits the inclination and the lateral position to the ADAS-ECU 3. The ADAS-ECU 3 is provided with the awakening degree determination apparatus, and determines the awakening degree based on the steering angle received from the EPS-ECU 1 and the inclination of the front and rear side of the subject vehicle with respect to the travel traffic lane of the subject vehicle and the lateral position of the subject vehicle in the travel traffic lane of the subject vehicle received from the white line recognition camera 2. When the ADAS-ECU 3 determines that the driver is in the drowsy state, the ADAS-ECU 3 transmits a command of sounding an alarm to the speaker 4. The speaker 4 sounds the alarm based on the command received from the ADAS-ECU.

As described above, the map data and the satellite positioning system or the map data and the LIDAR may be used instead of the white line recognition camera to detect the inclination of the front and rear side of the subject vehicle with respect to the travel traffic lane of the subject vehicle and the lateral position of the subject vehicle in the travel traffic lane of the subject vehicle. It is also applicable that the awakening degree determination apparatus is not mounted on the ADAS-ECU 3 but mounted on the EPS-ECU 1. When the awakening degree determination apparatus determines that the driver is in the drowsy state, the command may be transmitted to at least one of the display, the EPS-ECU, and the air conditioner instead of the speaker 4.

Figure 4:
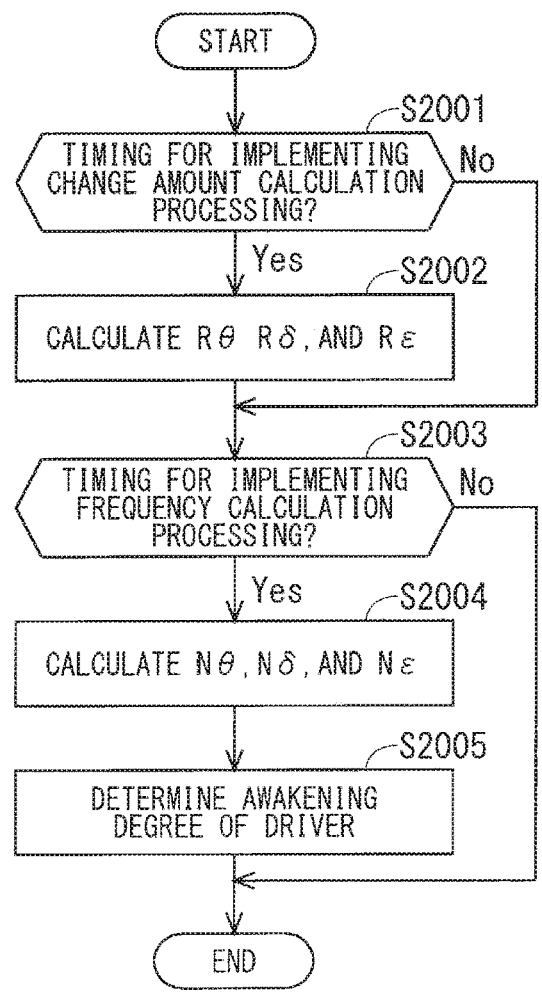
FIG. 4 A flow chart illustrating a procedure performed by the awakening degree determination apparatus according to the embodiment 2.

FIG. 4 is a flow chart illustrating a procedure of the awakening degree determination apparatus according to the present embodiment 2. Subjects of each determination in the following flow chart are not limited to those in the description described hereinafter, but may be any of constitutional elements of the awakening degree determination apparatus.

In Step S2001 in FIG. 4, the change amount calculation unit 210 determines whether a current time falls under a timing for implementing change amount calculation processing. An implementation cycle of the change amount calculation processing indicates a value equal to or smaller than target periods s$\theta$, s$\delta$, and s$\epsilon$ which are the first period, the second period, and the third period for calculating the angle change amount, the inclination change amount, and the position change amount, and is one-second cycle, for example. The implementation cycle of the procedure in FIG. 4 is shorter than the implementation cycle of the change amount calculation processing, and is 100 milliseconds, for example. When it is determined that the current time falls under the timing for implementing the change amount calculation processing, the processing proceeds to Step S2002, and when it is not determined that the current time falls under the timing for implementing the change amount calculation processing, the processing proceeds to Step S2003.

In Step S2002, the change amount calculation unit 210 calculates an angle change amount R$\theta$, an inclination change amount R$\delta$, and a position change amount R$\epsilon$. Subsequently, the processing proceeds to Step S2003.

In Step S2003, the frequency calculation unit 220 determines whether a current time falls under a timing for implementing frequency calculation processing. An implementation cycle of the frequency calculation processing indicates a value equal to or smaller than target periods t$\theta$, t$\delta$, and t$\epsilon$ for calculating the angle frequency, the inclination frequency, and the position frequency, and is ten-second cycle, for example. When it is determined that the current time falls under the timing for implementing the frequency calculation processing, the processing proceeds to Step S2004, and when it is not determined that the current time falls under the timing for implementing the frequency calculation processing, a calculation of a frequency in Step S2004 and a determination of an awakening degree in Step S2005 described hereinafter are not performed, but the procedure in FIG. 4 is finished.

In Step S2004, the frequency calculation unit 220 calculates an angle frequency N$\theta$ in which the angle change amount R$\theta$ exceeds a first threshold value Th$\theta$, an inclination frequency N$\delta$ in which the inclination change amount R$\delta$ exceeds a second threshold value Th$\delta$, and a position frequency N$\epsilon$ in which the position change amount R$\epsilon$ exceeds a third threshold value Th$\epsilon$.

In Step S2005, the awakening degree determination unit 230 determines the awakening degree of the driver based on the calculated angle frequency N$\theta$, inclination frequency N$\delta$, and position frequency N$\epsilon$. Subsequently, the procedure in FIG. 4 is finished.

Figure 5:
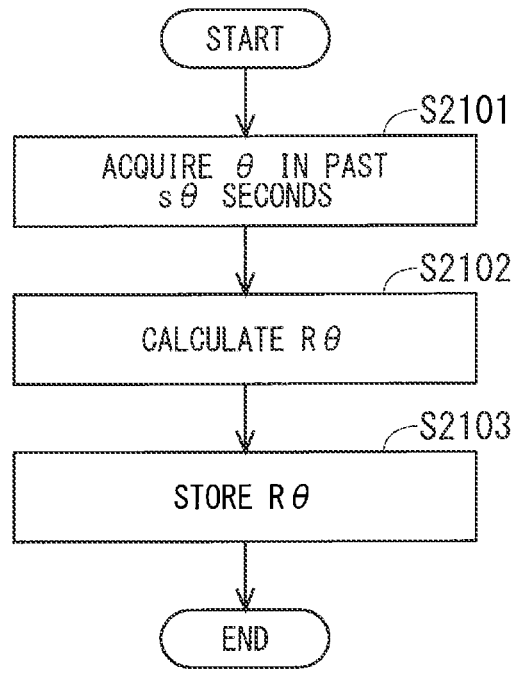
FIG. 5 A flow chart illustrating a procedure performed by the awakening degree determination apparatus according to the embodiment 2.

FIG. 5 is a flow chart illustrating the procedure of calculating the angle change amount R$\theta$ in the processing in Step S2002 in FIG. 4.

In Step S2101 in FIG. 5, the angle change amount calculation unit 211 acquires a steering angle $\theta$ over past s$\theta$ seconds from the steering angle detection unit 110. The se is two seconds, for example, by reason that a duration time of the corrected steering is substantially two seconds at most.

In Step S2102, the angle change amount calculation unit 211 calculates the angle change amount R$\theta$ over past s$\theta$ seconds based on the obtained steering angle $\theta$. The angle change amount R$\theta$ is calculated from a difference of values of the steering angles $\theta$ at two times different from each other during s$\theta$ seconds, and is calculated as a range of a difference between a maximum value and a minimum value, for example. In such a calculation, the angle change amount R$\theta$ in the case where the driver is in the awake state is 3 deg, for example, and the angle change amount R$\theta$ in the case where the driver is in the drowsy state is 12 deg, for example. Alternatively, the angle change amount R$\theta$ may be calculated as a difference between a third quartile point and a first quartile point of the steering angle $\theta$ in consideration of noise.

In Step S2103, the angle change amount calculation unit 211 stores the calculated angle change amount R$\theta$ in a buffer. The procedure in FIG. 5 is implemented on a cycle of the implementation of the change amount calculation processing, for example, on one-second cycle.

Figure 6:
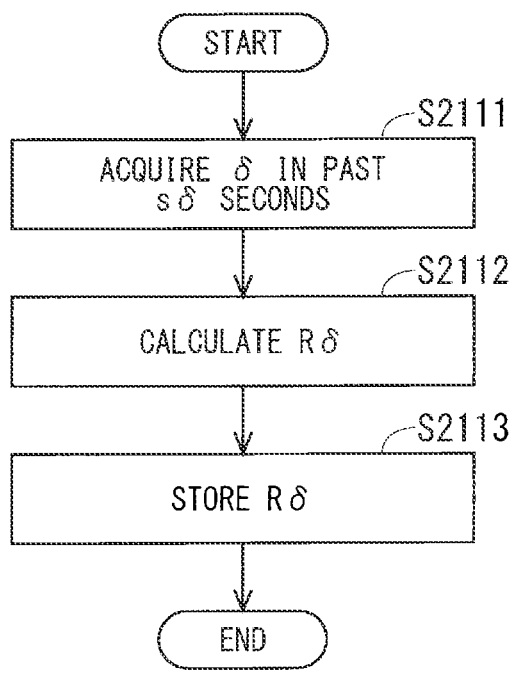
FIG. 6 A flow chart illustrating a procedure performed by the awakening degree determination apparatus according to the embodiment 2.

FIG. 6 is a flow chart illustrating the procedure of calculating the inclination change amount R$\delta$ in the processing in Step S2002 in FIG. 4.

Figure 7:
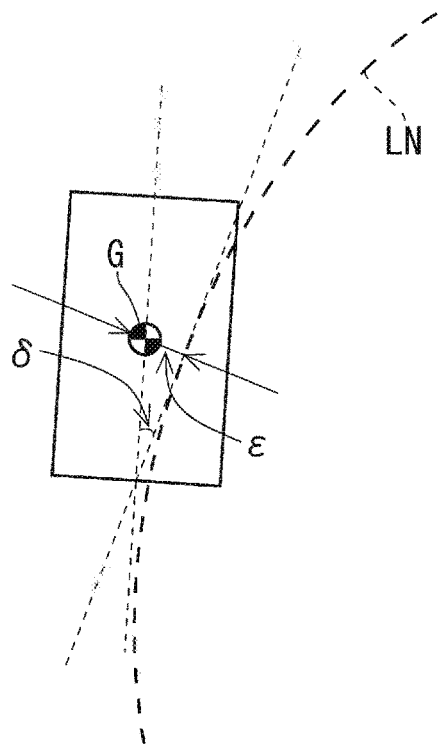
FIG. 7 A drawing for describing an inclination of a front and rear side of a subject vehicle with respect to a travel traffic lane of the subject vehicle and a lateral position of the subject vehicle in the travel traffic lane of the subject vehicle.

In Step S2111 in FIG. 6, the inclination change amount calculation unit 212 acquires an inclination $\delta$ of the front and rear side of the subject vehicle with respect to the travel traffic lane of the subject vehicle over past s$\delta$ seconds from the inclination detection unit 120. The s$\delta$ is two seconds, for example, based on a cycle in which the inclination $\delta$ of the front and rear side of the subject vehicle takes an extreme value. Herein, the inclination $\delta$ of the front and rear side of the subject vehicle is defined by an angle between a tangent line at a nearest point in a median line LN of the travel traffic lane of the subject vehicle with respect to a gravity G of the subject vehicle and a forward direction of the subject vehicle as illustrated in FIG. 7, for example. Alternatively, the inclination $\delta$ of the front and rear side of the subject vehicle may also be defined by an angle between a tangent line of a median line of the travel traffic lane of the subject vehicle at a forward gazing point and a forward direction of the subject vehicle, for example.

In Step S2112, the inclination change amount calculation unit 212 calculates the inclination change amount R$\delta$ over past s$\delta$ seconds based on the acquired inclination $\delta$. The inclination change amount R$\delta$ is calculated from a difference of values of the inclination $\delta$ at two times different from each other during s$\theta$ seconds, and is calculated as a range, for example. In such a calculation, the inclination change amount R$\delta$ in the case where the driver is in the awake state is 1.5 deg, for example, and the inclination change amount R$\delta$ in the case where the driver is in the drowsy state is 4 deg, for example. Alternatively, the inclination change amount R$\delta$ may be calculated as a difference between a third quartile point and a first quartile point of the inclination $\delta$ in consideration of noise.

In Step S2113, the inclination change amount calculation unit 212 stores the calculated inclination change amount Rδ in a buffer. The procedure in FIG. 6 is implemented on a cycle of the implementation of the change amount calculation processing, for example, on one-second cycle.

Figure 8:
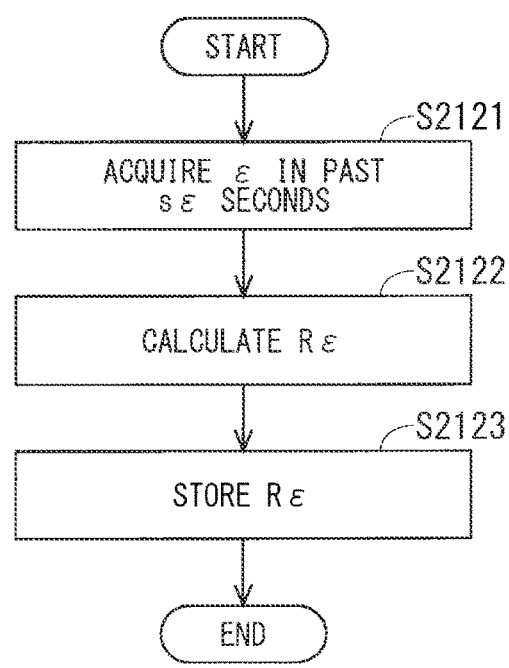
FIG. 8 A flow chart illustrating a procedure performed by the awakening degree determination apparatus according to the embodiment 2.

FIG. 8 is a flow chart illustrating the procedure of calculating the position change amount Rε in the processing in Step S2002 in FIG. 4.

In Step S2121 in FIG. 8, the position change amount calculation unit 213 acquires a lateral position ε of the subject vehicle in the travel traffic lane of the subject vehicle over past sε seconds from the lateral position detection unit 130. The sε is five seconds based on a meandering cycle, for example. Herein, the lateral position ε of the subject vehicle is defined by a distance from a gravity G of the subject vehicle to a median line LN of the travel traffic lane of the subject vehicle as illustrated in FIG. 7, for example. Alternatively, the lateral position ε of the subject vehicle may be defined by a distance from a center of the subject vehicle or a position where the white line recognition camera is disposed to a median line of the travel traffic lane of the subject vehicle.

In Step S2122, the position change amount calculation unit 213 calculates the position change amount Rε over past sε seconds based on the acquired lateral position ε. The position change amount Rε is calculated from a difference of values of the lateral position ε at two times different from each other during sc seconds, and is calculated as a range, for example. In such a calculation, the position change amount Rε in the case where the driver is in the awake state is 1 m, for example, and the position change amount Rε in the case where the driver is in the drowsy state is 3 m, for example. Alternatively, the position change amount Rε may be calculated as a difference between a third quartile point and a first quartile point of the lateral position s in consideration of noise.

In Step S2123, the position change amount calculation unit 213 stores the calculated position change amount Rε in a buffer. The procedure in FIG. 8 is implemented on a cycle of the implementation of the change amount calculation processing, for example, on one-second cycle.

Figure 9:
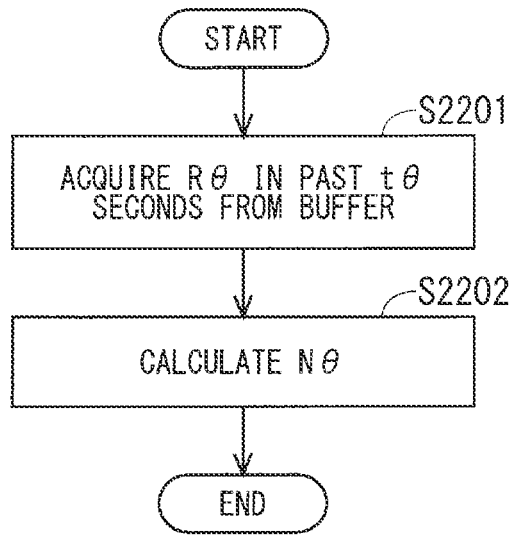
FIG. 9 A flow chart illustrating a procedure performed by the awakening degree determination apparatus according to the embodiment 2.

FIG. 9 is a flow chart illustrating the procedure of calculating the angle frequency Nθ in which the angle change amount Rθ exceeds the first threshold value Thθ in the processing in Step S2004 in FIG. 4.

In Step S2201 in FIG. 9, the angle frequency calculation unit 211 acquires a plurality of angle change amounts Rθ over past tθ seconds from the buffer. The tθ is sixty seconds based on a duration time of a short-time reduction in the awakening degree, for example.

In Step S2202, the angle frequency calculation unit 221 counts the number of the plurality of angle change amounts Rθ in tθ seconds, which are acquired from the buffer, exceeding the first threshold value Thθ, thereby calculating the angle frequency Nθ. The first threshold value Thθ is 6 deg, which is larger than the angle change amount Rθ in the awake state, for example. In such a first threshold value Thθ, the angle frequency Nθ in the case where the driver is in the awake state is two, for example, and the angle frequency Nθ in the case where the driver is in the drowsy state is eight, for example. The procedure in FIG. 9 is implemented on a cycle of the implementation of the frequency calculation processing, for example, on ten-second cycle.

Figure 10:
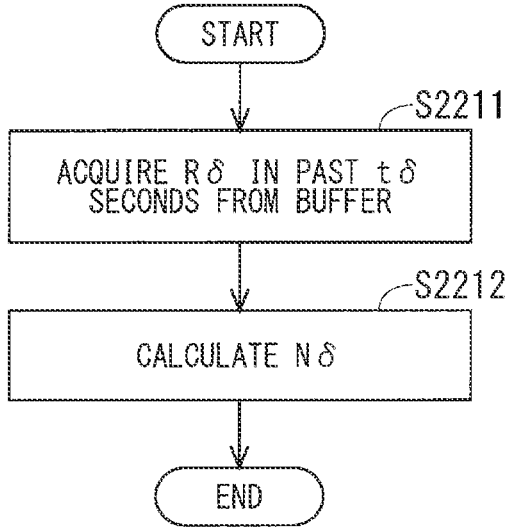
FIG. 10 A flow chart illustrating a procedure performed by the awakening degree determination apparatus according to the embodiment 2.

FIG. 10 is a flow chart illustrating the procedure of calculating the inclination frequency Nδ in which the inclination change amount Rδ exceeds the second threshold value Thδ in Step S2004 in FIG. 4.

In Step S2211 in FIG. 10, the inclination frequency calculation unit 222 acquires a plurality of inclination change amounts Rδ over past tδ seconds from the buffer. The tδ is sixty seconds based on a duration time of a short-time reduction in the awakening degree, for example.

In Step S2212, the inclination frequency calculation unit 222 counts the number of the plurality of inclination change amounts Rδ in tδ seconds, which are acquired from the buffer, exceeding the second threshold value Thδ, thereby calculating the inclination frequency Nδ. The second threshold value Thδ is 2 deg, which is larger than the inclination change amount Rδ in the awake state, for example. In such a second threshold value Thδ, the inclination frequency Nθ in the case where the driver is in the awake state is two, for example, and the inclination frequency Nδ in the case where the driver is in the drowsy state is six, for example. The procedure in FIG. 10 is implemented on a cycle of the implementation of the frequency calculation processing, for example, on ten-second cycle.

Figure 11:
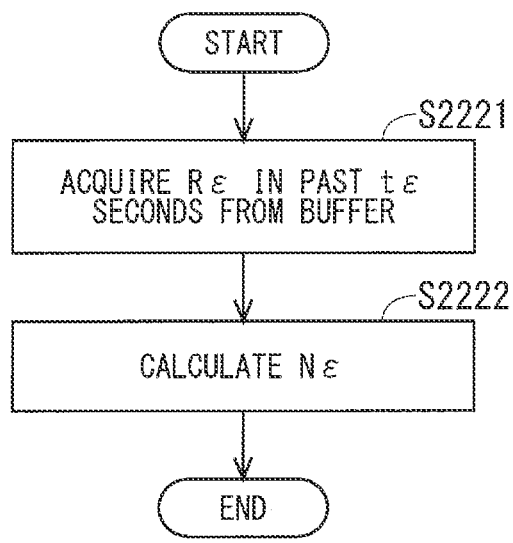
FIG. 11 A flow chart illustrating a procedure performed by the awakening degree determination apparatus according to the embodiment 2.

FIG. 11 is a flow chart illustrating the procedure of calculating the position frequency Nε in which the position change amount Rε exceeds the third threshold value Thε in Step S2004 in FIG. 4.

In Step S2221 in FIG. 11, the position frequency calculation unit 223 acquires a plurality of position change amounts Rε over past to seconds from the buffer. The tε is sixty seconds based on a duration time of a short-time reduction in the awakening degree, for example.

In Step S2222, the position frequency calculation unit 223 counts the number of the plurality of position change amounts Rε in tε seconds, which are acquired from the buffer, exceeding the third threshold value Thε, thereby calculating the position frequency Nε. The third threshold value Thε is 1.8 m, which is larger than the position change amount Rε in the awake state, for example. In such a third threshold value Thε, the position frequency Nε in the case where the driver is in the awake state is zero, for example, and the position frequency Nε in the case where the driver is in the drowsy state is six, for example. The procedure in FIG. 11 is implemented on a cycle of the implementation of the frequency calculation processing, for example, on ten-second cycle.

Figure 12:
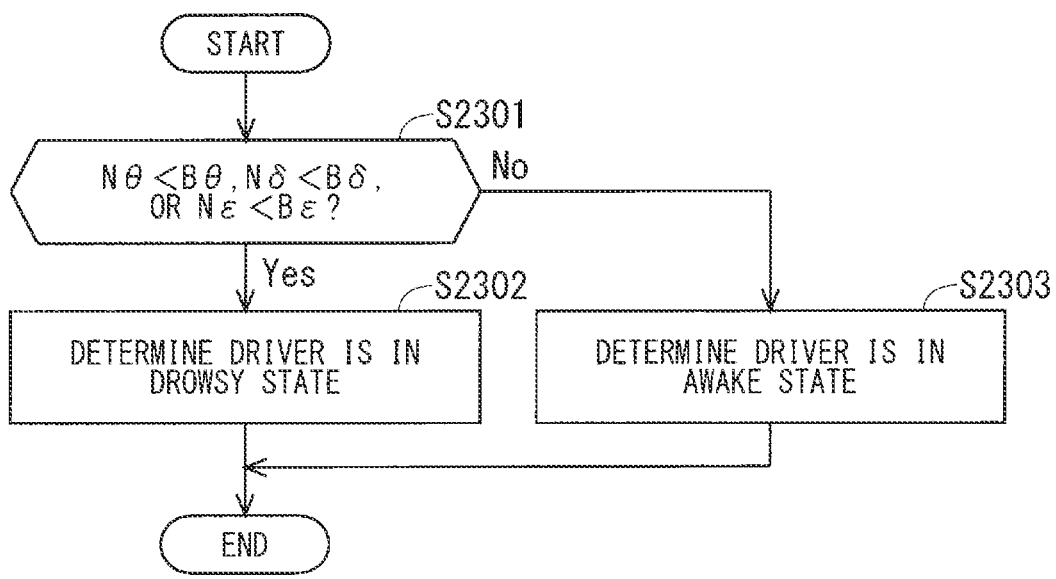
FIG. 12 A flow chart illustrating a procedure performed by the awakening degree determination apparatus according to the embodiment 2.

FIG. 12 is a flow chart illustrating the procedure of determining the awakening degree which is the processing in Step S2005 in FIG. 4.

In Step 2301 in FIG. 12, the awakening degree determination unit 230 determines whether the angle frequency Nθ exceeds the fourth threshold value Bθ, whether the inclination frequency Nδ exceeds the fifth threshold value Bδ, and whether the position frequency Nε exceeds the sixth threshold value Bε. The fourth threshold value Bθ is 4, which is larger than the angle frequency Nθ in the awake state, for example, the fifth threshold value Bδ is 4, which is larger than the inclination frequency Nδ in the awake state, for example, and the sixth threshold value Bε is 4, which is larger than the position frequency Nε in the awake state, for example. When it is determined that at least one of the angle frequency Nθ, the inclination frequency Nδ, and the position frequency Nε exceeds the threshold value, the processing proceeds to Step S2302, and when it is determined that none of there exceeds the threshold value, the processing proceeds to Step S2303.

In Step S2302, the awakening degree determination unit 230 determines that the awakening degree of the driver of the subject vehicle decreases and the driver is in the drowsy state. Subsequently, the procedure in FIG. 12 is finished. In the meanwhile, in Step S2303, the awakening degree determination unit 230 determines that the awakening degree of the driver of the subject vehicle does not decrease and the driver is in the awake state. The procedure in FIG. 12 is implemented on a cycle of the implementation of the frequency calculation processing, for example, on ten-second cycle.

Figure 13:
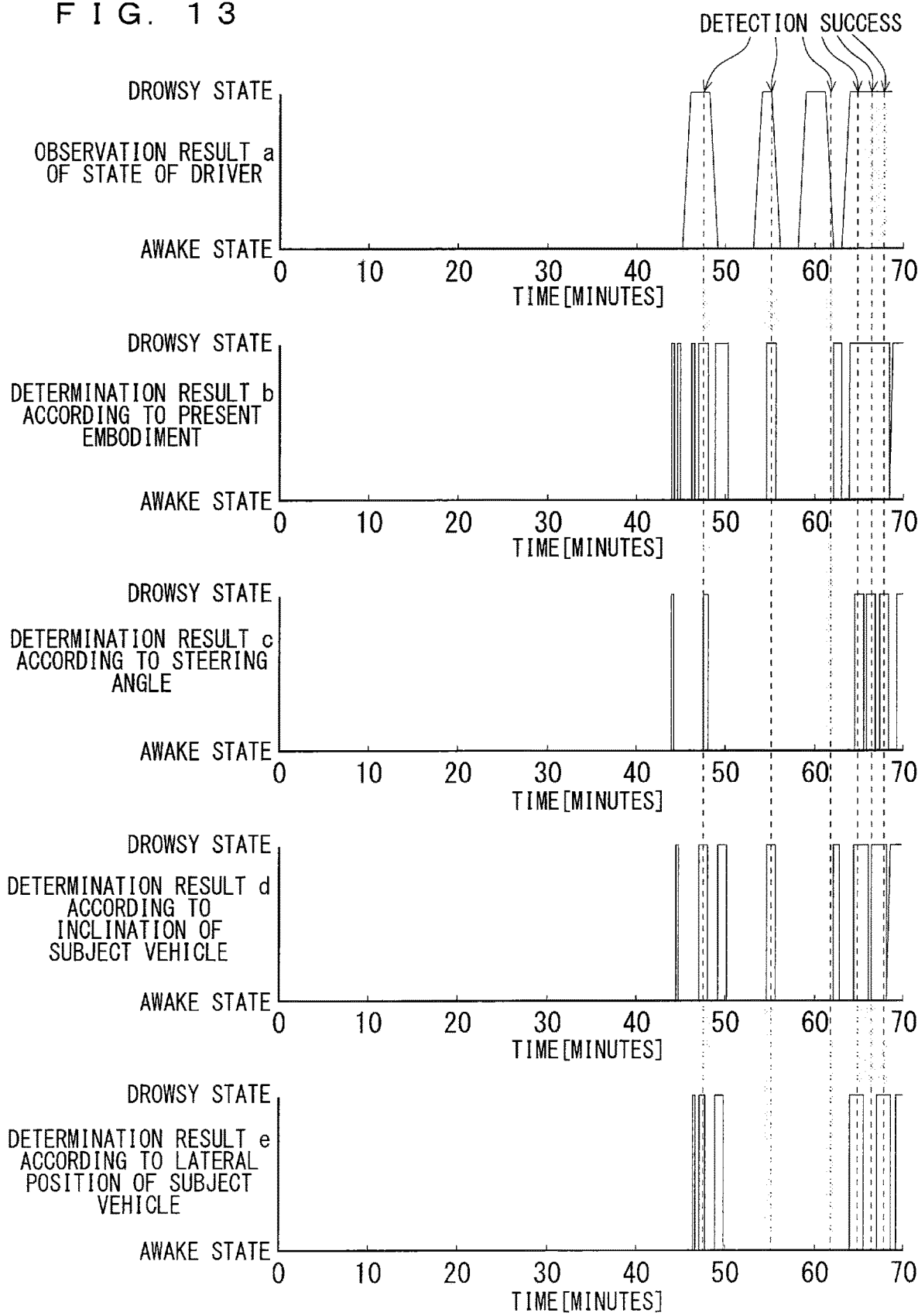
FIG. 13 A drawing illustrating an experimental result of the awakening degree determination apparatus according to the embodiment 2.
Figure 14:
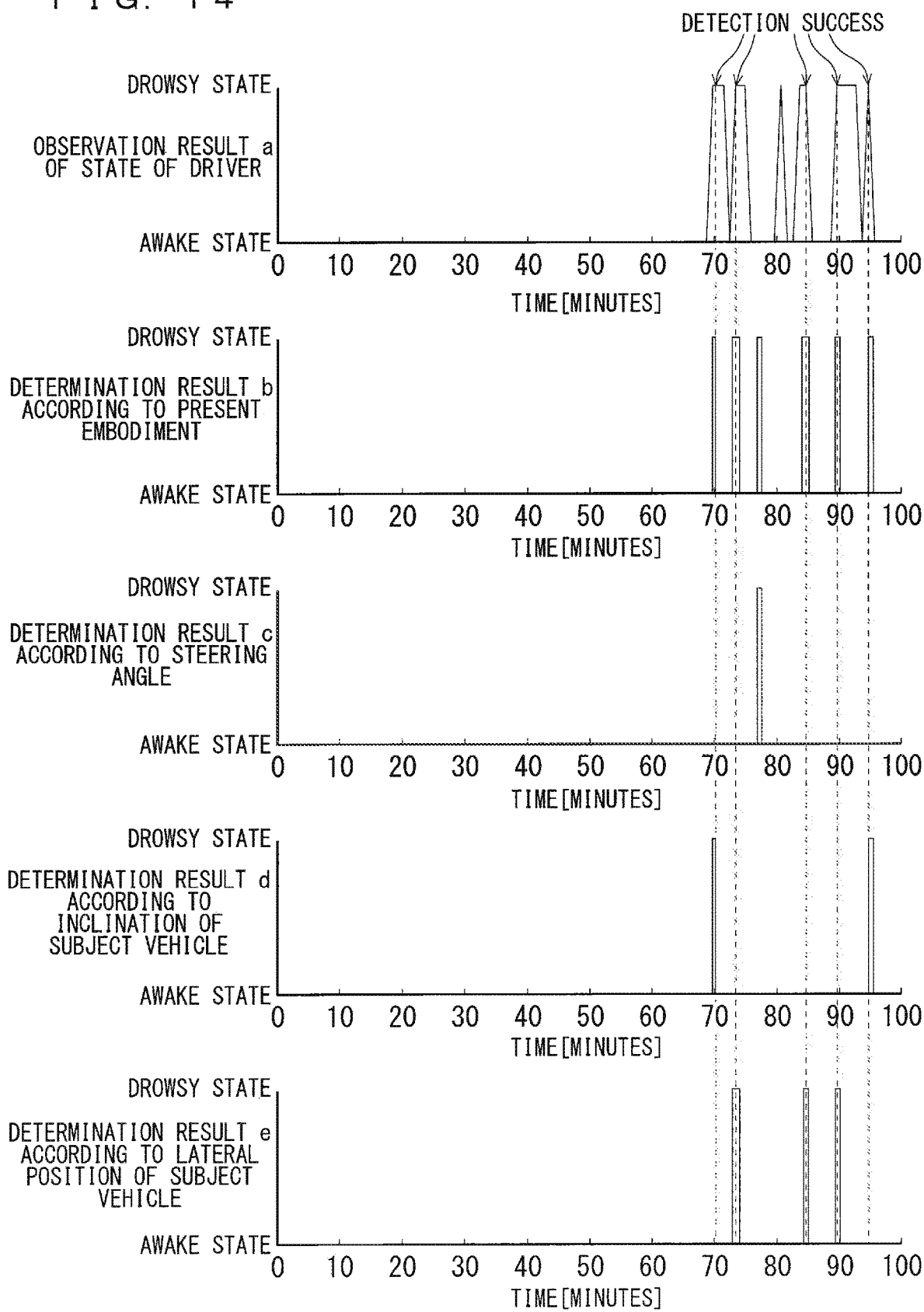
FIG. 14 A drawing illustrating an experimental result of the awakening degree determination apparatus according to the embodiment 2.

Next, an experimental result in a case where the driver enters the drowsy state from the awake state is described using FIG. 13 and FIG. 14. Each of FIG. 13 and FIG. 14 illustrates an observation result a of a state of the driver, a determination result b according to the present embodiment 1, a determination result c in a case of using only the steering angle (only the angle frequency), a determination result d in a case of using only the inclination of the front and rear side of the subject vehicle with respect to the travel traffic lane of the subject vehicle (only the inclination frequency), and a determination result e in a case of using only the lateral position of the subject vehicle in the travel traffic lane of the subject vehicle (only the position frequency), as a time series graph.

In FIG. 13, the driver was in the drowsy state where the corrected steering and the meandering occurred. As shown in the determination result b in FIG. 13, according to the determination in the present embodiment 1 in which the steering angle, the inclination of the front and rear side of the subject vehicle with respect to the travel traffic lane of the subject vehicle, and the lateral position of the subject vehicle with respect to the travel traffic lane of the subject vehicle are integrated, the drowsy state can be roughly detected.

In FIG. 14, the driver was in the drowsy state where the corrected steering did not occur but only the meandering occurred. A comparison between the determination result c and the observation result a in FIG. 14 shows that the drowsy state cannot be correctly determined in the case of using only the steering angle. A comparison between the determination results d and e and the observation result a in FIG. 14 shows that the drowsy state which cannot be determined in the case of using only the steering angle is determined in the case of using only the inclination of the front and rear side of the subject vehicle with respect to the travel traffic lane of the subject vehicle and the case of using only the lateral position of the subject vehicle with respect to the travel traffic lane of the subject vehicle. Thus, according to the present embodiment 1 capable of integrating these three indexes, a detection accuracy of the drowsy state can be improved compared with a detection accuracy in the case of solely using each index.

Outline of Embodiment 2

According to the awakening degree determination apparatus according to the present embodiment 2, the awakening degree is determined based on the frequency in which each change amount of the steering angle, the inclination of the front and rear side of the subject vehicle with respect to the travel traffic lane of the subject vehicle, and the lateral position of the subject vehicle in the travel traffic lane of the subject vehicle exceeds the threshold value. Such a configuration enables an independent evaluation of the presence or absence of the corrected steering and the presence or absence of the meandering, for example, thus can appropriately meet the drive pattern in the reduction in the awakening degree of the driver (in the drowsy state) which differs widely between individuals such as the presence or absence of the pulsating corrected steering and the presence or absence of the meandering. Thus, the awakening degree can be accurately determined. According to the present embodiment 2, also acquired is an effect that the pulsating corrected steering can be detected more easily by evaluating the magnitude of the fluctuation of the steering angle, for example, in accordance with the change amount as typified by the range than by evaluating the magnitude of the fluctuation of the steering angle, for example, in accordance with a variance or a standard variation, for example.

Embodiment 3

For example, there is a case where the while line recognition camera cannot detect, due to backlight, for example, the inclination of the front and rear side of the subject vehicle with respect to the travel traffic lane of the subject vehicle and the lateral position of the subject vehicle in the travel traffic lane of the subject vehicle, thereby not being able to determine the awakening degree. Thus, in order to determine the awakening degree as much as possible, it is also applicable that the awakening degree is determined by only the angle frequency in which the change amount of the steering angle, that is to say, the angle change amount exceeds the first threshold value Thθ as illustrated in an embodiment 3 of the present invention described hereinafter.

Figure 15:
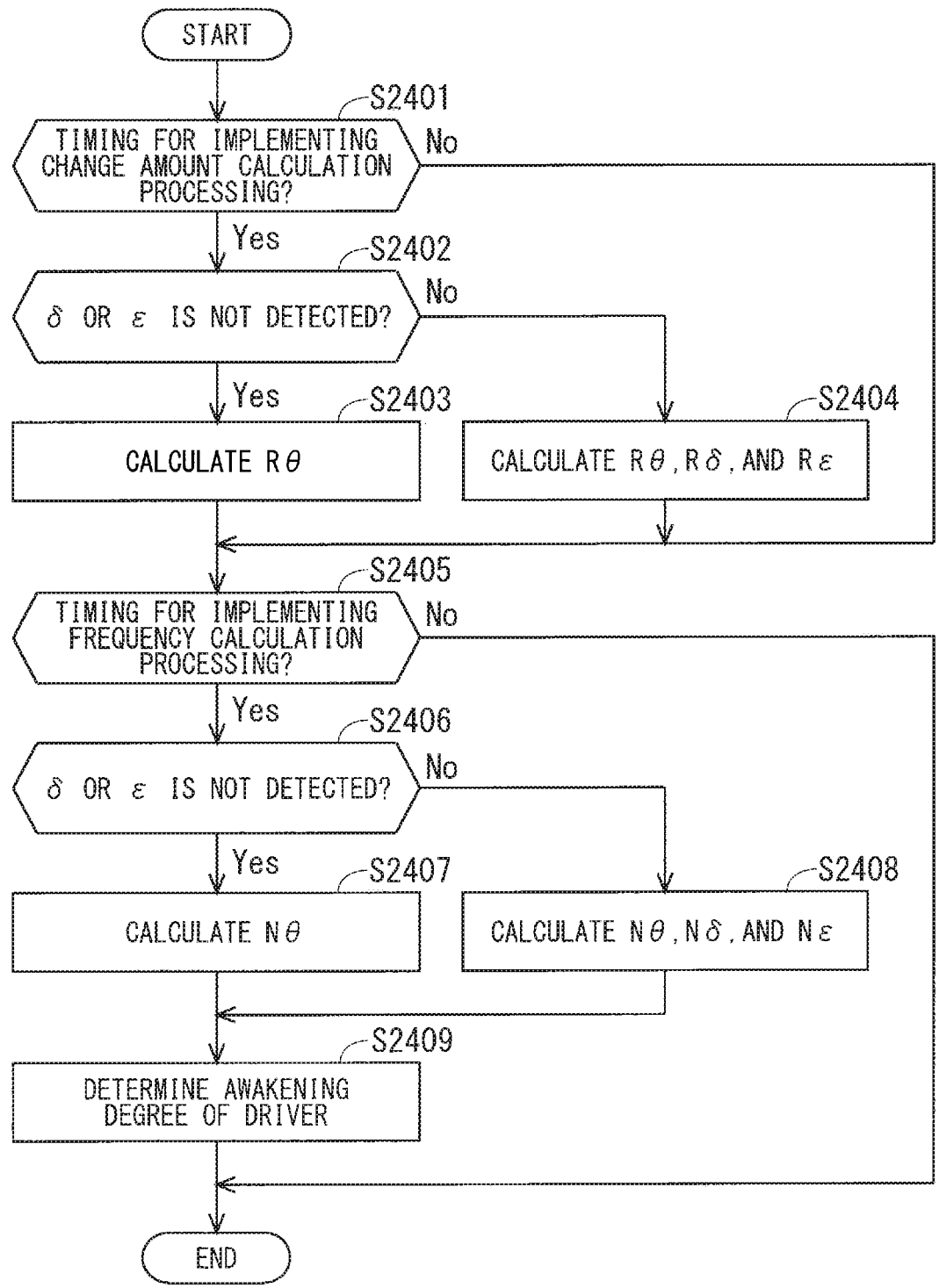
FIG. 15 A flow chart illustrating a procedure performed by an awakening degree determination apparatus according to an embodiment 3.

FIG. 15 is a flow chart illustrating a procedure of an awakening degree determination apparatus according to the present embodiment 3. The same reference numerals as those described in the present embodiment 3 will be assigned to the same or similar constituent elements described above, and the different constituent elements are mainly described hereinafter.

In Step S2401 in FIG. 15, the change amount calculation unit 210 determines whether a current time falls under a timing for implementing change amount calculation processing. An implementation cycle of the change amount calculation processing indicates a value equal to or smaller than target periods $s\theta$, $s\delta$, and $s\varepsilon$ for calculating the angle change amount, the inclination change amount, and the position change amount, and is one-second cycle, for example. When it is determined that the current time falls under the timing for implementing the change amount calculation processing, the processing proceeds to Step S2402, and when it is not determined that the current time falls under the timing for implementing the change amount calculation processing, the processing proceeds to Step S2405.

In Step S2402, the change amount calculation unit 210 determines whether the inclination detection unit 120 and the lateral position detection unit 130 can detect the inclination $\delta$ of the front and rear side of the subject vehicle and the lateral position $\varepsilon$ of the subject vehicle. When it is determined that at least one of the inclination $\delta$ and the lateral position $\varepsilon$ cannot be detected, the processing proceeds to Step S2403, and when it is determined that both of them can be detected, the processing proceeds to Step S2404.

In Step S2403, the change amount calculation unit 210 calculates only the angle change amount Rθ. Subsequently, the processing proceeds to Step S2405.

In the meanwhile, in Step S2404, the change amount calculation unit 210 calculates the angle change amount Rθ, the inclination change amount Rδ, and the position change amount Rε. Subsequently, the processing proceeds to Step S2405.

In Step S2405, the frequency calculation unit 220 determines whether a current time falls under a timing for implementing frequency calculation processing. An implementation cycle of the frequency calculation processing indicates a value equal to or smaller than the target periods tθ, tδ, and tε for calculating the angle frequency, the inclination frequency, and the position frequency, and is ten-second cycle, for example. When it is determined that the current time falls under the timing for implementing the frequency calculation processing, the processing proceeds to Step S2406, and when it is not determined that the current time falls under the timing for implementing the frequency calculation processing, the calculation of the frequency and the determination of the awakening degree are not performed, but the procedure in FIG. 15 is finished.

In Step S2406, the frequency calculation unit 220 determines whether the inclination detection unit 120 and the lateral position detection unit 130 can detect the inclination δ of the front and rear side of the subject vehicle and the lateral position a of the subject vehicle. When it is determined that at least one of the inclination δ and the lateral position ε cannot be detected, the processing proceeds to Step S2407, and when it is determined that both of them can be detected, the processing proceeds to Step S2408.

In Step S2407, the frequency calculation unit 220 calculates the angle frequency Nθ. Subsequently, the processing proceeds to Step S2409.

In the meanwhile, in Step S2408, the frequency calculation unit 220 calculates the angle frequency Nθ, the inclination frequency Nδ, and the position frequency Nε. Subsequently, the processing proceeds to Step S2409.

In Step S2409, the awakening degree determination unit 230 determines the awakening degree of the driver based on the calculated frequencies. Subsequently, the procedure in FIG. 15 is finished.

The calculation of the change amount in Step S2403 and Step S2404 is appropriately performed in accordance with the procedures illustrated in FIG. 5, FIG. 6, and FIG. 8, for example. The calculation of the frequency in Step S2407 and Step S2408 is appropriately performed in accordance with the procedures illustrated in FIG. 9, FIG. 10, and FIG. 11, for example. The determination of the awakening degree in Step S2409 is performed in accordance with the procedure illustrated in FIG. 12, for example.

Outline of Embodiment 3

According to the awakening degree determination apparatus in the present embodiment 3 described above, the awakening degree determination unit 230 determines that the awakening degree decreases when the change amount calculation unit 210 cannot acquire the inclination change amount or the position change amount and the angle frequency exceeds the fourth threshold value Bθ. According to such a configuration, the awakening degree can be determined even in the case where the inclination of the front and rear side of the subject vehicle and the lateral position of the subject vehicle cannot be detected.

Embodiment 4

For example, there is a case, depending on a shape of a road in the travel traffic lane of the subject vehicle, for example, the angle change amount in the case where the driver is in the awake state, is substantially the same as the angle change amount in the case where the driver is in the drowsy state, for example. Thus, in order to reduce an influence thereof, it is applicable to calculate the angle change amount Rθ, the inclination change amount Rδ, and the position change amount Rε only when a curvature change of the travel traffic lane of the subject vehicle is small.

Figure 16:
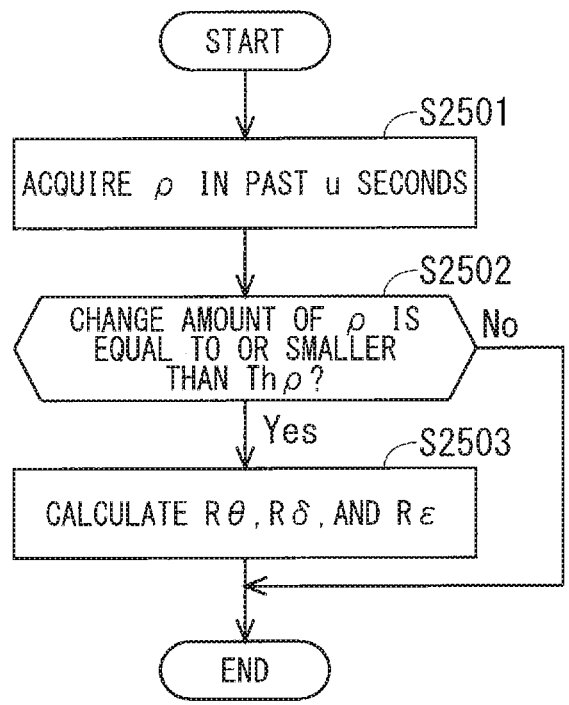
FIG. 16 A flow chart illustrating a procedure performed by an awakening degree determination apparatus according to an embodiment 4.

FIG. 16 is a flow chart illustrating a procedure of calculating the angle change amount Rθ, the inclination change amount Rδ, and the position change amount Rε in consideration of a curvature ρ of the travel traffic lane of the subject vehicle. The same reference numerals as those described in the present embodiment 4 will be assigned to the same or similar constituent elements described above, and the different constituent elements are mainly described hereinafter.

In Step S2501 in FIG. 16, the change amount calculation unit 210 calculates the curvature ρ of the travel traffic lane of the subject vehicle detected for u seconds, which is a past predetermined period, using the while line recognition camera. The u is three seconds, for example, in consideration of a period in which information such as the angle change amount is influenced by the curvature change.

In Step S2502, the change amount calculation unit 210 determines whether a change amount of the curvature ρ which is a difference between a maximum value max (ρ) and a minimum value min (ρ) in the past u seconds is equal to or smaller than a predetermined threshold value Thρ. The threshold value Thρ is a value indicating that the subject vehicle can travel along a traffic lane having a curvature changed without an occurrence of a sudden steering and a lateral wobble, and is Thρ=2.2×10$^{-3}$ m$^{-1}$ at 100 km per hour based on a relationship between a design speed in Government Order on Road Design Standards and a curvature radius. When it is determined that the change amount of the curvature ρ is equal to or smaller than the threshold value Thρ, the processing proceeds to Step S2503, and when it is determined that the change amount of the curvature ρ is not equal to or smaller than the threshold value Thρ, the angle change amount Rθ is not calculated, for example, but the procedure in FIG. 16 is finished.

In Step S2503, the change amount calculation unit 210 calculates the angle change amount Rθ, the inclination change amount Rδ, and the position change amount Rε. Subsequently, the procedure in FIG. 16 is finished. The calculation of the change amount in Step S2503 is performed in accordance with the procedures illustrated in FIG. 5, FIG. 6, and FIG. 8, for example. The threshold value Thρ may be changed in accordance with a speed of the subject vehicle.

Outline of Embodiment 4

According to the awakening degree determination apparatus in the present embodiment 4 described above, the angle change amount Rθ, the inclination change amount Rδ, and the position change amount Rε are calculated only when the curvature change of the travel traffic lane of the subject vehicle in the predetermined period u is equal to or smaller than the predetermined threshold value. According to such a configuration, the influence of the steering of the subject vehicle and the vehicle movement caused by the shape of the road can be reduced, and the awakening degree can be accurately determined.

Embodiment 5

In order to reduce the influence of a lane change and right and left turn, as the embodiment 5 of the present invention described hereinafter, the angle change amount Rθ, the inclination change amount Rδ, and the position change amount Rε may also be calculated only when a direction indicator of the subject vehicle, that is to say, a turn signal indicator of the subject vehicle is in an off-state.

Figure 17:
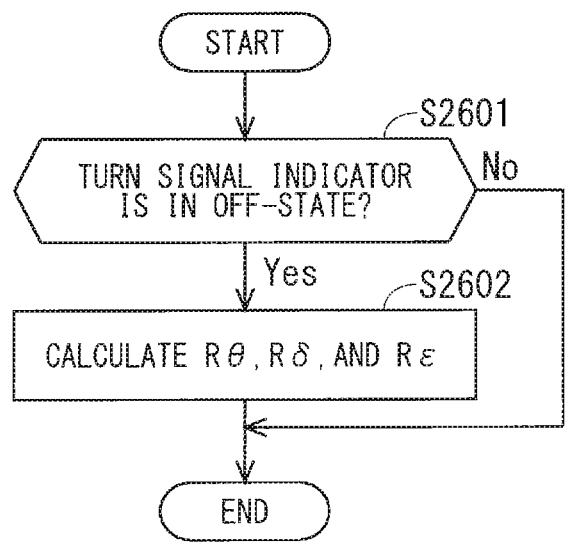
FIG. 17 A flow chart illustrating a procedure performed by an awakening degree determination apparatus according to an embodiment 5.

FIG. 17 is a flow chart illustrating a procedure of calculating the angle change amount Rθ, the inclination change amount Rδ, and the position change amount Rε in consideration of a state of the turn signal indicator. The same reference numerals as those described in the present embodiment 5 will be assigned to the same or similar constituent elements described above, and the different constituent elements are mainly described hereinafter.

In Step S2601 in FIG. 17, the change amount calculation unit 210 determines whether the turn signal indicator is in the off-state. When it is determined that the turn signal indicator is in the off-state, the processing proceeds to Step S2602, and when it is determined that the turn signal indicator is in an on-state, the angle change amount Rθ is not calculated, for example, but the procedure in FIG. 17 is finished.

In Step S2602, the change amount calculation unit 210 calculates the angle change amount Rθ, the inclination change amount Rδ, and the position change amount Rε. Subsequently, the procedure in FIG. 17 is finished. The calculation of the change amount in Step S2602 is performed in accordance with the procedures illustrated in FIG. 5, FIG. 6, and FIG. 8, for example.

Outline of Embodiment 5

According to the awakening degree determination apparatus in the present embodiment 4 described above, the angle change amount Rθ, the inclination change amount Rδ, and the position change amount Rε are calculated only when the turn signal indicator of the subject vehicle is in the off-state. According to such a configuration, the influence of the lane change of the subject vehicle, the steering for the right and left turn, and the vehicle movement can be reduced, and the awakening degree can be accurately determined.

Embodiment 6

The awakening degree determination apparatus according to an embodiment 6 of the present invention determines the first threshold value Thθ, the second threshold value Thδ, and the third threshold value Thε based on individual information on a drive technique or a drive property of the driver. The individual information includes, for example, the angle change amount Rε in the target period sθ in the predetermined fourth period after a driving of the subject vehicle is started, the inclination change amount Rδ in the target period sδ in the fourth period, and the position change amount Rε in the target period se in the fourth period. The fourth period is 600 seconds in which the driver is not supposed to enter the drowsy state.

Figure 18:
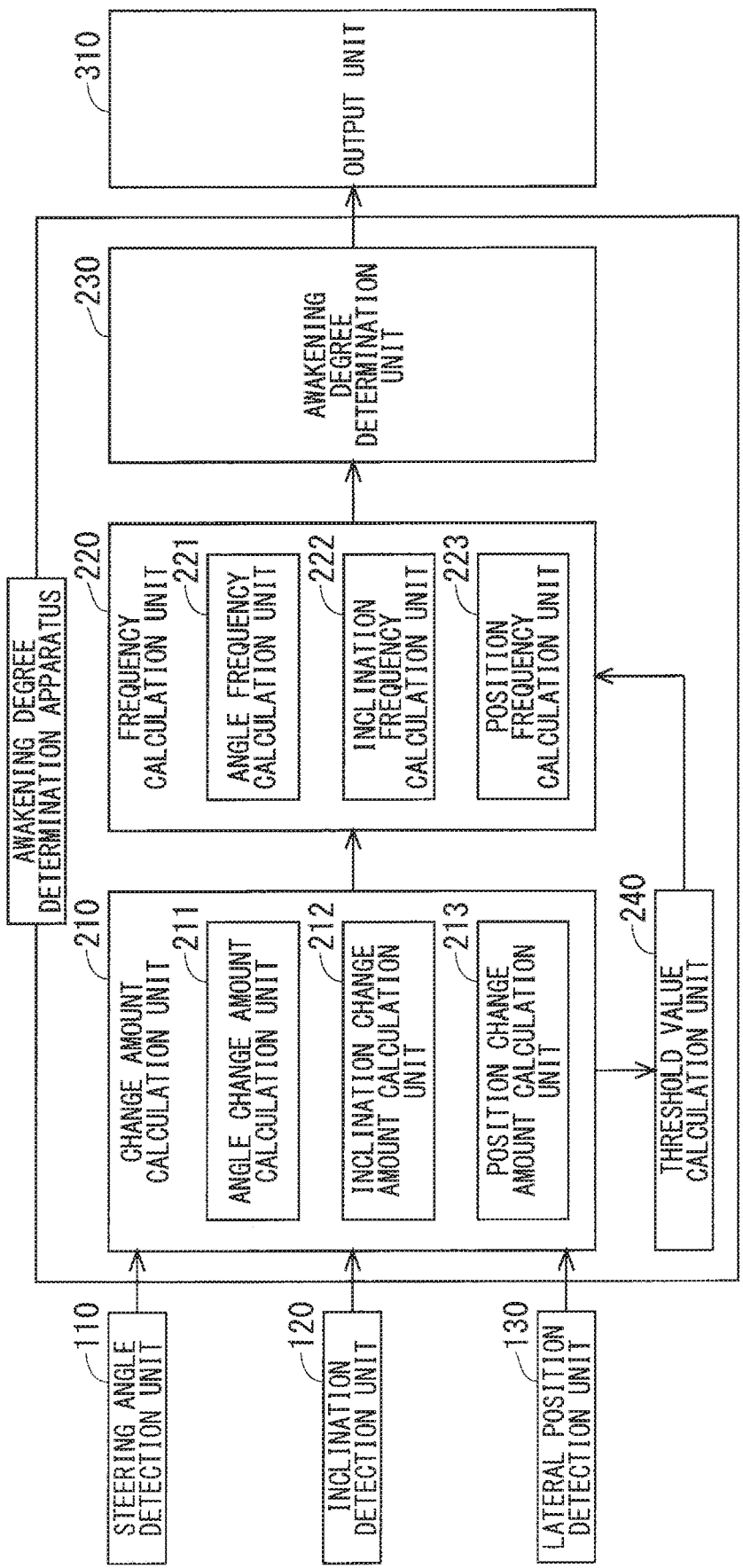
FIG. 18 A block diagram illustrating a schematic configuration of an awakening degree determination apparatus according to an embodiment 6.

FIG. 18 is a block diagram illustrating a schematic configuration of the awakening degree determination apparatus according to the present embodiment 6. The same reference numerals as those described in the present embodiment 6 will be assigned to the same or similar constituent elements described above, and the different constituent elements are mainly described hereinafter.

The awakening degree determination apparatus according to the present embodiment 6 is the same as the awakening degree determination apparatus described in the embodiment 2 to which a threshold value calculation unit 240 is added. The threshold value calculation unit 240 is a calculation unit calculating a threshold value based on the change amount calculated in the change amount calculation unit 210. The threshold value calculation unit 240 regressively determines the first threshold value Thθ based on an average value ave (θ) which is an average value of the angle change amounts Rθ in the fourth period. In the similar manner, the threshold value calculation unit 240 regressively determines the second threshold value Thδ based on an inclination average value ave (δ) which is an average value of the inclination change amounts Rδ in the fourth period, and regressively determines the third threshold value Thε based on a position average value ave (ε) which is an average value of the position change amounts Rε in the fourth period. This processing may also be performed in the change amount calculation unit 210, the frequency calculation unit 220, or the awakening degree determination unit 230.

Figure 19:
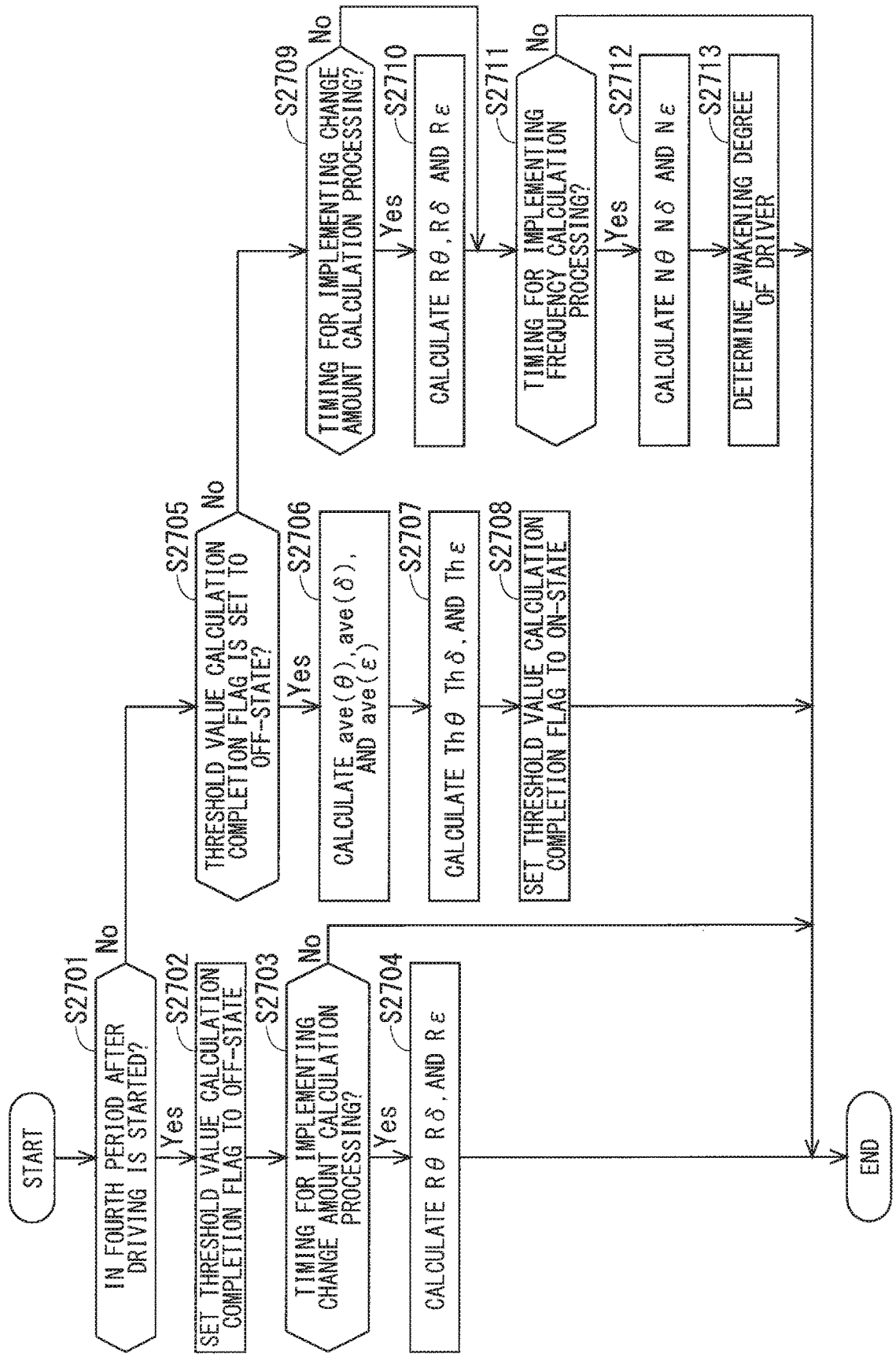
FIG. 19 A flow chart illustrating a procedure performed by the awakening degree determination apparatus according to the embodiment 6.

FIG. 19 is a flow chart illustrating a procedure of determining the first threshold value Thθ, the second threshold value Thδ, and the third threshold value Thε based on the individual information on the drive technique or the drive property of the driver.

In Step S2701 in FIG. 19, the change amount calculation unit 210 determines whether a current time is in the fourth period after the driving of the subject vehicle is started. When it is determined that the current time is in the fourth period, the processing proceeds to Step S2702, and when it is not determined that the current time is in the fourth period, the processing proceeds to Step S2705.

In Step S2702, the change amount calculation unit 210 sets a threshold value calculation completion flag to an off-state.

In Step S2703, the change amount calculation unit 210 determines whether a current time falls under a timing for implementing change amount calculation processing. An implementation cycle of the change amount calculation processing indicates a value equal to or smaller than target periods sθ, sδ, and sε for calculating the angle change amount, the inclination change amount, and the position change amount, and is one-second cycle, for example. When it is determined that the current time falls under the timing for implementing the change amount calculation processing, the processing proceeds to Step S2704, and when it is not determined that the current time falls under the timing for implementing the change amount calculation processing, the angle change amount Rθ is not calculated, for example, but the procedure in FIG. 19 is finished.

In Step S2704, the change amount calculation unit 210 calculates the angle change amount Rθ, the inclination change amount Rδ, and the position change amount Rε. Subsequently, the procedure in FIG. 19 is finished.

In Step S2705, the threshold value calculation unit 240 determines whether the threshold value calculation completion flag is set to the off-state. When it is determined that the threshold value calculation completion flag is set to the off-state, the processing proceeds to Step S2706, and when it is determined that the threshold value calculation completion flag is set to an on-state, the processing proceeds to Step S2709.

In Step S2706, the threshold value calculation unit 240 calculates the angle average value ave (θ), the inclination average value ave (δ), and the position average value ave (ε).

In Step S2707, the threshold value calculation unit 240 regressively calculates the first threshold value Thθ, the second threshold value Thδ, and the third threshold value Thε from the angle average value ave (θ), the inclination average value ave (δ), and the position average value ave (ε).

In Step S2708, the threshold value calculation unit 240 sets a threshold value calculation completion flag to the on-state. Subsequently, the procedure in FIG. 19 is finished.

In Step S2709, the change amount calculation unit 210 determines whether a current time falls under a timing for implementing change amount calculation processing. When it is determined that the current time falls under the timing for implementing the change amount calculation processing, the processing proceeds to Step S2710, and when it is not determined that the current time falls under the timing for implementing the change amount calculation processing, the angle change amount $R\theta$ is not calculated, for example, but the processing proceeds to Step S2711.

In Step S2710, the change amount calculation unit 210 calculates the angle change amount $R\theta$, the inclination change amount $R\delta$, and the position change amount $R\varepsilon$. Subsequently, the processing proceeds to Step S2711.

In Step S2711, the frequency calculation unit 220 determines whether a current time falls under a timing for implementing frequency calculation processing. When it is determined that the current time falls under the timing for implementing the frequency calculation processing, the processing proceeds to Step S2712, and when it is not determined that the current time falls under the timing for implementing the frequency calculation processing, the calculation of the frequency and the determination of the awakening degree are not performed, but the procedure in FIG. 19 is finished.

In Step S2712, the frequency calculation unit 220 calculates the angle frequency $N\theta$ in which the angle change amount $R\theta$ exceeds the first threshold value $Th\theta$, the inclination frequency $N\delta$ in which the inclination change amount $R\delta$ exceeds the second threshold value $Th\delta$, and the position frequency $N\varepsilon$ in which the position change amount $R\varepsilon$ exceeds a third threshold value $Th\varepsilon$.

In Step S2713, the awakening degree determination unit 230 determines the awakening degree of the driver based on the calculated angle frequency $N\theta$, inclination frequency $N\delta$, and position frequency $N\varepsilon$. Subsequently, the procedure in FIG. 19 is finished.

Figure 20:
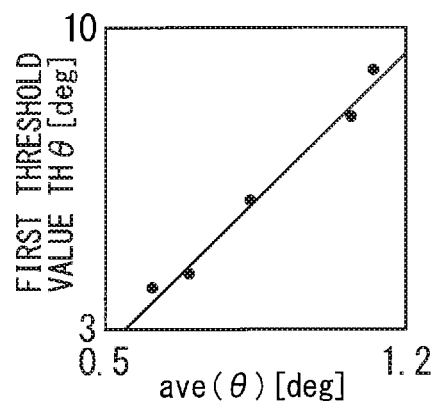
FIG. 20 A drawing illustrating a relationship between an average value of angle change amounts after a driving is started and an appropriate value of a first threshold value.
Figure 21:
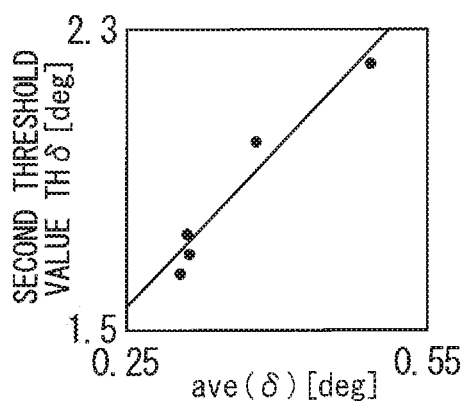
FIG. 21 A drawing illustrating a relationship between an average value of inclination change amounts after a driving, is started and an appropriate value of a second threshold value.
Figure 22:
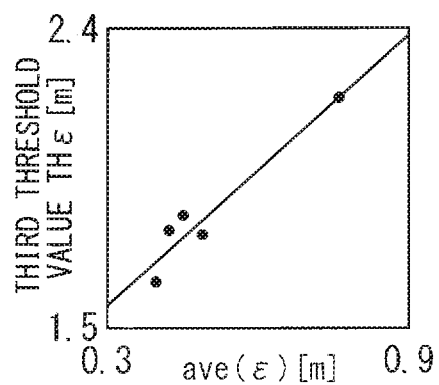
FIG. 22 A drawing illustrating a relationship between an average value of position change amounts after a driving is started and an appropriate value of a third threshold value.

Described next using FIG. 20 to FIG. 22 is the regressive determination of the first threshold value $Th\theta$, the second threshold value $Th\delta$, and the third threshold value $Th\varepsilon$.

FIG. 20 is a drawing in which the average value ave ($\theta$) of the angle change amounts $R\theta$ in 600 seconds after the driving is started for five drivers and an appropriate value of the first threshold value $Th\theta$ for each driver are plotted. The appropriate value of the first threshold value $Th\theta$ is a value experimentally determined from experimental data. A straight line in FIG. 20 is a regression line. FIG. 20 shows that there is a linear relationship between the angle average value ave ($\theta$) and the appropriate value of the first threshold value $Th\theta$ for each driver, thus the threshold value calculation unit 240 can regressively determine the first threshold value $Th\theta$ from the angle average value ave ($\theta$).

FIG. 21 is a drawing in which the average value ave ($\delta$) of the inclination change amounts $R\delta$ in 600 seconds after the driving is started for five drivers and an appropriate value of the second threshold value $Th\delta$ for each driver are plotted. The appropriate value of the second threshold value $Th\delta$ is a value experimentally determined from experimental data. A straight line in FIG. 21 is a regression line. FIG. 21 shows that there is a linear relationship between the inclination average value ave ($\delta$) and the appropriate value of the second threshold value $Th\delta$ for each driver, thus the threshold value calculation unit 240 can regressively determine the second threshold value $Th\delta$ from the inclination average value ave ($\delta$).

FIG. 22 is a drawing in which the average value ave ($\varepsilon$) of the position change amounts $R\varepsilon$ in 600 seconds after the driving is started for five drivers and an appropriate value of the third threshold value $Th\varepsilon$ for each driver are plotted. The appropriate value of the third threshold value $Th\varepsilon$ is a value experimentally determined from experimental data. A straight line in FIG. 22 is a regression line. FIG. 22 shows that there is a linear relationship between the position average value ave ($\varepsilon$) and the appropriate value of the third threshold value $Th\varepsilon$ for each driver, thus the threshold value calculation unit 240 can regressively determine the third threshold value $Th\varepsilon$ from the position average value ave ($\varepsilon$).

Outline of Embodiment 6

The awakening degree determination apparatus according to the present embodiment 6 described above determines the first threshold value $Th\theta$, the second threshold value $Th\delta$, and the third threshold value $Th\varepsilon$ based on individual information on the drive technique or the drive property of the driver. According to such a configuration, the influence of the individual difference of the drive technique can be reduced, and the awakening degree can be accurately determined.

Embodiment 7

It is also applicable that, in calculating the angle change amount $R\theta$, the inclination change amount $R\delta$, and the position change amount $R\varepsilon$, each change amount is not calculated from each time-series data which is buffered, but a maximum value and a minimum value are sequentially updated for each period of the first period, the second period, and the third period to calculate the angle change amount $R\theta$, the inclination change amount $R\delta$, and the position change amount $R\varepsilon$.

Figure 23:
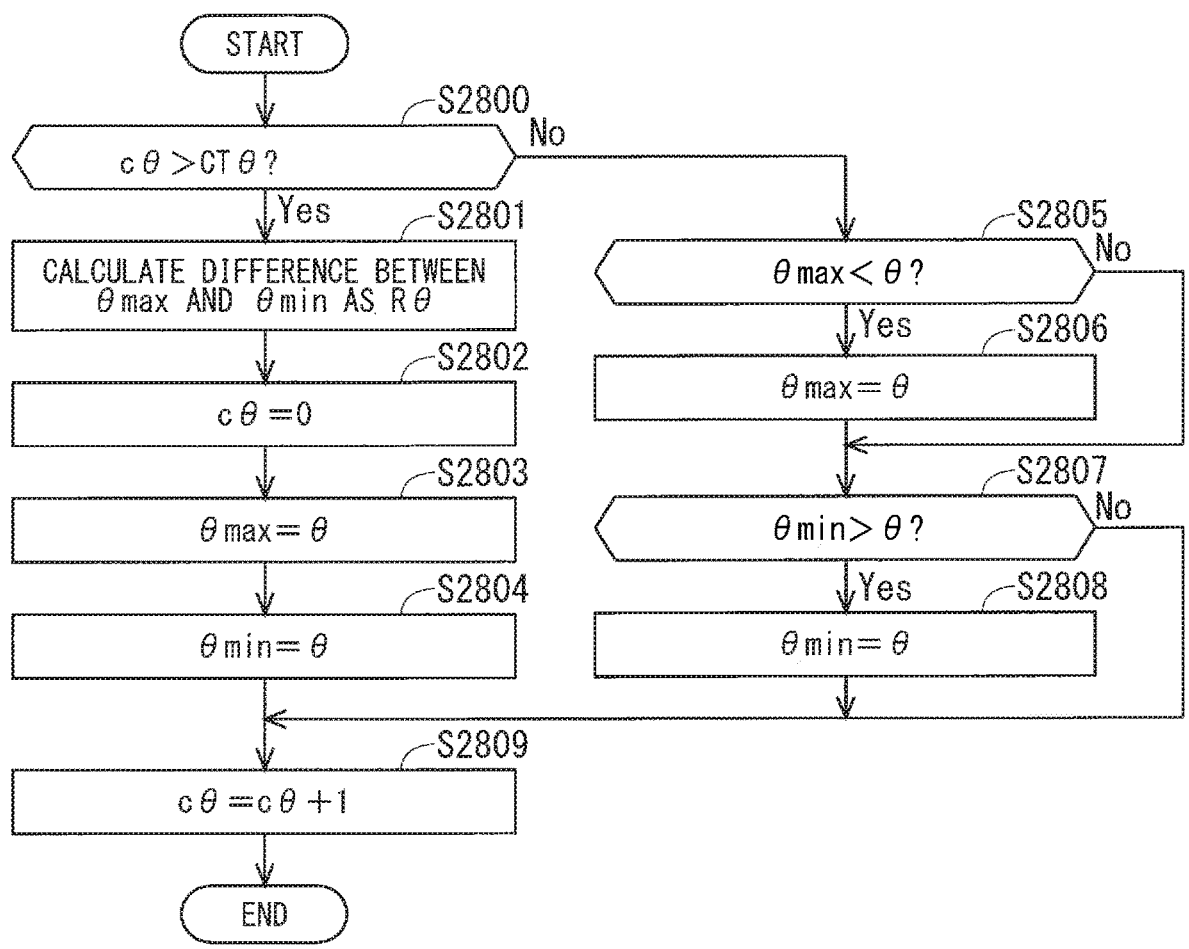
FIG. 23 A flow chart illustrating a procedure performed by an awakening degree determination apparatus according to an embodiment 7.

FIG. 23 is a flow chart illustrating the procedure of sequentially updating a maximum value $\theta$ max and a minimum value $\theta$ min of the steering angle $\theta$ to calculate the angle change amount $R\theta$. The same reference numerals as those described in the present embodiment 7 will be assigned to the same or similar constituent elements described above, and the different constituent elements are mainly described hereinafter.

In Step S2800 in FIG. 23, the change amount calculation unit 210 determines whether a counter $c\theta$ is larger than a predetermined threshold value $CT\theta$. The threshold value $CT\theta$ is a product of a period se and a sampling rate $f\theta$ of the steering angle, for example. When the counter $c\theta$ is larger than the threshold value $CT\theta$, the processing proceeds to Step S2801, and when the counter $c\theta$ is equal to or smaller than the threshold value $CT\theta$, the processing proceeds to Step S2805.

In Step S2801, the change amount calculation unit 210 calculates the angle change amount $R\theta$ by taking a difference between the maximum value $\theta$ max and the minimum value $\theta$ min which are stored at that time.

In Step S2802, the change amount calculation unit 210 initializes the counter $c\theta$ to zero. The change amount calculation unit 210 stores a value of a current steering angle $\theta$ in the maximum value $\theta$ max in Step S2803, and stores the value in the minimum value $\theta$ min in Step S2804. Subsequently, the processing proceeds to Step S2809.

In Step S2805, the change amount calculation unit 210 determines whether the maximum value $\theta$ max stored at that time is smaller than the value of the current steering angle $\theta$. When it is determined that the maximum value $\theta$ max is smaller, the processing proceeds to Step S2806, and when it is not determined that the maximum value $\theta$ max is smaller, the processing proceeds to Step S2807. In Step S2806, the change amount calculation unit 210 updates the maximum value θ max to the current steering angle θ. Subsequently, the processing proceeds to Step S2807.

In Step S2807, the change amount calculation unit 210 determines whether the minimum value θ min stored at that time is larger than the value of the current steering angle θ. When it is determined that the minimum value θ min is larger, the processing proceeds to Step S2808, and when it is not determined that the minimum value θ min is larger, the processing proceeds to Step S2809. In Step S2808, the change amount calculation unit 210 updates the minimum value θ min to the current steering angle θ. Subsequently, the processing proceeds to Step S2809.

In Step S2809, the change amount calculation unit 210 increments the value of the counter cθ. Subsequently, the procedure in FIG. 23 is finished.

Figure 24:
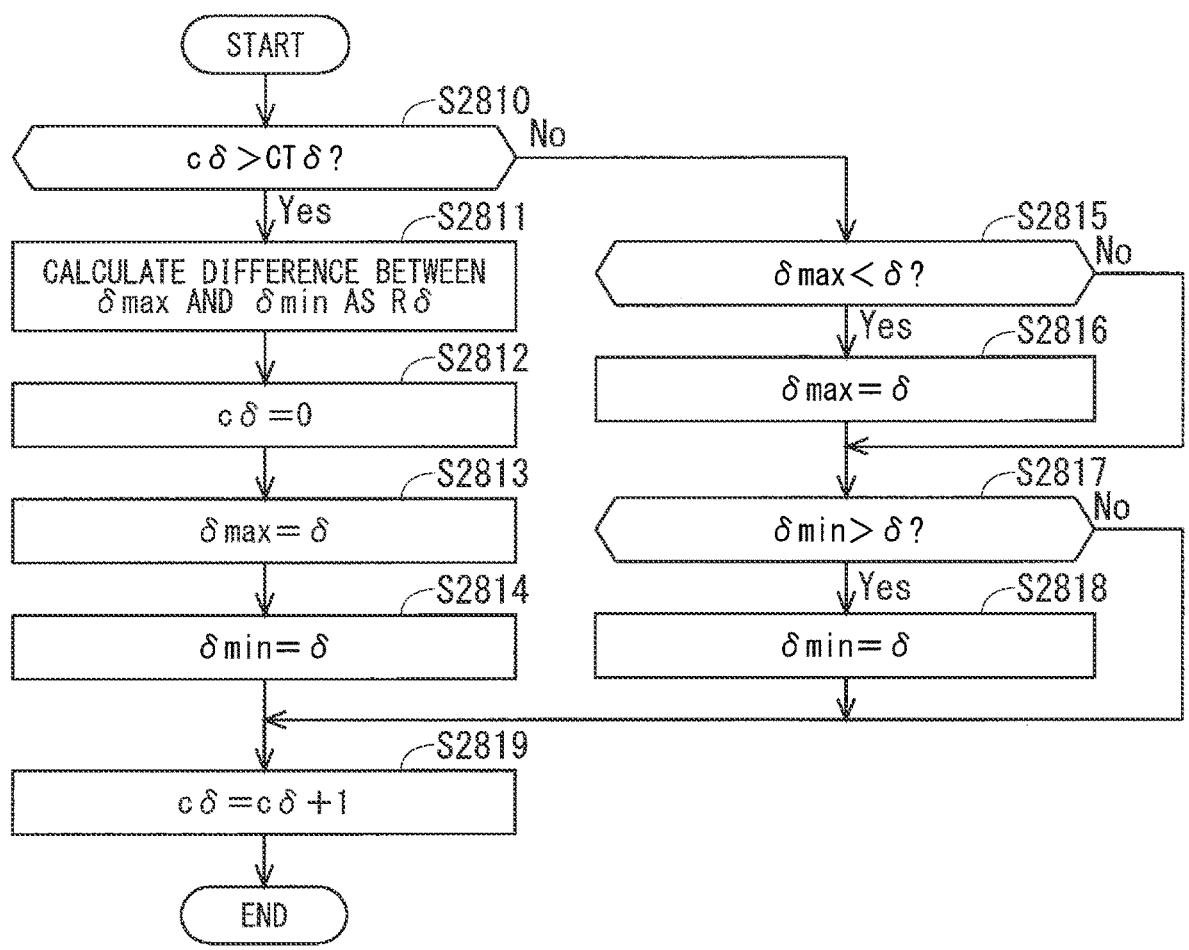
FIG. 24 A flow chart illustrating a procedure performed by an awakening degree determination apparatus according to an embodiment 7.

FIG. 24 is a flow chart illustrating a procedure of sequentially updating a maximum value δ max and a minimum value δ min of the inclination δ of the front and rear side of the subject vehicle with respect to the travel traffic lane of the subject vehicle to calculate the inclination change amount Rδ.

In Step S2810 in FIG. 24, the change amount calculation unit 210 determines whether a counter cδ is larger than a predetermined threshold value CTδ. The threshold value CTδ is a product of a period sδ and a sampling rate fδ of the inclination δ of the front and rear side of the subject vehicle, for example. When the counter cδ is larger than the threshold value CTδ, the processing proceeds to Step S2811, and when the counter cδ is equal to or smaller than the threshold value CTδ, the processing proceeds to Step S2815.

In Step S2811, the change amount calculation unit 210 calculates the inclination change amount Rδ by taking a difference between the maximum value δ max and the minimum value δ min which are stored at that time.

In Step S2812, the change amount calculation unit 210 initializes the counter cδ to zero. The change amount calculation unit 210 stores a value of a current inclination δ of the front and rear side of the subject vehicle in the maximum value δ max in Step S2813, and stores the value in the minimum value δ min in Step S2814. Subsequently, the processing proceeds to Step S2819.

In Step S2815, the change amount calculation unit 210 determines whether the maximum value δ max stored at that time is smaller than the value of the current inclination δ of the front and rear side of the subject vehicle. When it is determined that the maximum value δ max is smaller, the processing proceeds to Step S2816, and when it is not determined that the maximum value δ max is smaller, the processing proceeds to Step S2817. In Step S2816, the change amount calculation unit 210 updates the value δ max to the current inclination δ of the front and rear side of the subject vehicle. Subsequently, the processing proceeds to Step S2817.

In Step S2817, the change amount calculation unit 210 determines whether the minimum value δ min stored at that time is larger than the value of the current inclination δ of the front and rear side of the subject vehicle. When it is determined that the minimum value δ min is larger, the processing proceeds to Step S2818, and when it is not determined that the minimum value δ min is larger, the processing proceeds to Step S2819. In Step S2818, the change amount calculation unit 210 updates the minimum value δ min to the current inclination δ of the front and rear side of the subject vehicle. Subsequently, the processing proceeds to Step S2819.

In Step S2819, the change amount calculation unit 210 increments the value of the counter cδ. Subsequently, the procedure in FIG. 24 is finished.

Figure 25:
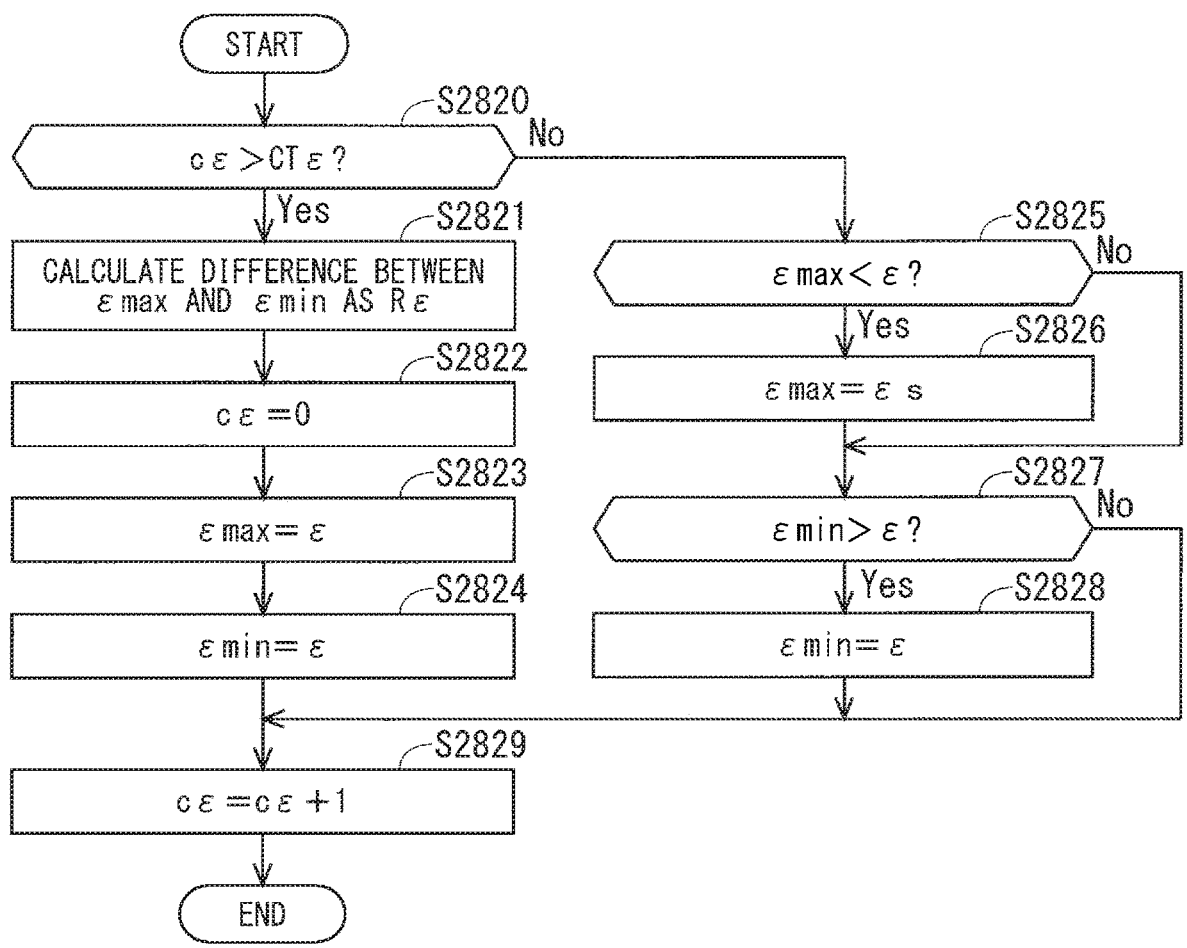
FIG. 25 A flow chart illustrating a procedure performed by the awakening degree determination apparatus according to the embodiment 7.

FIG. 25 is a flow chart illustrating a procedure of sequentially updating a maximum value ε max and a minimum value ε min of the lateral position ε of the subject vehicle in the travel traffic lane of the subject vehicle to calculate the position change amount Rε.

In Step S2820 in FIG. 25, the change amount calculation unit 210 determines whether a counter ca is larger than a predetermined threshold value CTε. The threshold value CTε is a product of a period sε and a sampling rate fε of the lateral position ε of the subject vehicle, for example. When the counter ca is larger than the threshold value CTε, the processing proceeds to Step S2821, and when the counter cε is equal to or smaller than the threshold value CTε, the processing proceeds to Step S2825.

In Step S2821, the change amount calculation unit 210 calculates the position change amount Rε by taking a difference between the maximum value ε max and the minimum value ε min which are stored at that time.

In Step S2822, the change amount calculation unit 210 initializes the counter cε to zero. The change amount calculation unit 210 stores a value of a current lateral position ε of the subject vehicle in the maximum value ε max in Step S2823, and stores the value in the minimum value ε min in Step S2824. Subsequently, the processing proceeds to Step S2829.

In Step S2825, the change amount calculation unit 210 determines whether the maximum value ε max stored at that time is smaller than the value of the current lateral position ε of the subject vehicle. When it is determined that the maximum value ε max is smaller, the processing proceeds to Step S2826, and when it is not determined that the maximum value ε max is smaller, the processing proceeds to Step S2827. In Step S2826, the change amount calculation unit 210 updates the maximum value ε max to the current lateral position ε of the subject vehicle. Subsequently, the processing proceeds to Step S2827.

In Step S2827, the change amount calculation unit 210 determines whether the minimum value min stored at that time is larger than the value of the current lateral position ε of the subject vehicle. When it is determined that the minimum value ε min is larger, the processing proceeds to Step S2828, and when it is not determined that the minimum value ε min is larger, the processing proceeds to Step S2829. In Step S2828, the change amount calculation unit 210 updates the minimum value ε min to the current lateral position ε of the subject vehicle. Subsequently, the processing proceeds to Step S2829.

In Step S2829, the change amount calculation unit 210 increments the value of the counter cε. Subsequently, the procedure in FIG. 25 is finished.

Outline of Embodiment 7

According to the awakening degree determination apparatus of the present embodiment 7 described above, the maximum value and the minimum value are sequentially updated for each period of the first period, the second period, and the third period to calculate the angle change amount Rθ, the inclination change amount Rδ, and the position change amount Rε. According to such a configuration, the buffered data can be reduced when each change amount is calculated, thus a used amount of a memory can be reduced.

Another Modification Example

Figure 26:
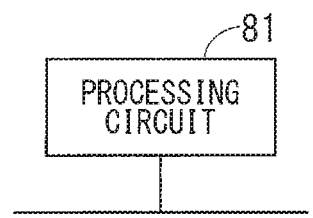
FIG. 26 A block diagram illustrating a hardware configuration of an awakening degree determination apparatus according to a modification example.

The change amount acquisition unit 21, the frequency calculation unit 22, and the awakening degree determination unit 23 illustrated in FIG. 1 descried above are referred to as "the change amount acquisition unit 21 etc." hereinafter. The change amount acquisition unit 21 etc. is achieved by a processing circuit 81 illustrated in FIG. 26. That is to say, the processing circuit 81 includes the change amount acquisition unit 21 acquiring the angle change amount, the inclination change amount, and the position change amount, the frequency calculation unit 22 calculating the angle frequency, the inclination frequency, and the position frequency, and the awakening degree determination unit 23 determining that the awakening degree of the driver of the subject vehicle decreases when at least one of the angle frequency, the inclination frequency, and the position frequency exceeds the fourth threshold value, the fifth threshold value, and the sixth threshold value. Dedicated hardware may be applied to the processing circuit 81, or a processor executing a program stored in a memory may also be applied. Examples of the processor include a central processing unit, a processing device, an arithmetic device, a microprocessor, a microcomputer, or a digital signal processor (DSP).

When the processing circuit 81 is the dedicated hardware, a single circuit, a complex circuit, a programmed processor, a parallel-programmed processor, an application specific integrated circuit (ASIC), a field-programmable gate array (FPGA), or a combination of them, for example, falls under the processing circuit 81. Each function of the change amount acquisition unit 21 etc. may be achieved by circuits to which the processing circuit is dispersed, or each function of them may also be collectively achieved by one processing circuit.

Figure 27:
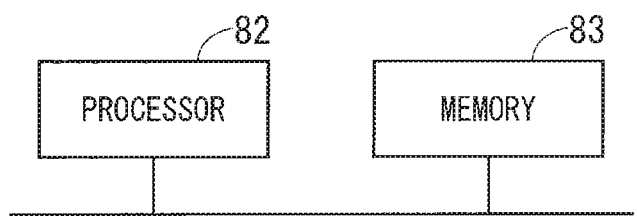
FIG. 27 A block diagram illustrating a hardware configuration of an awakening degree determination apparatus according to a modification example.

When the processing circuit 81 is the processor, the functions of the change amount acquisition unit 21 etc. are achieved by a combination with software etc. Software, firmware, or software and firmware, for example, fall under the software etc. The software etc. is described as a program and is stored in a memory 83. As illustrated in FIG. 27, a processor 82 applied to the processing circuit 81 reads out and executes a program stored in the memory 83, thereby achieving the function of each unit. That is to say, the awakening degree determination apparatus includes the memory 83 to store the program to resultingly execute, at a time of being executed by the processing circuit 81, steps of: acquiring the angle change amount, the inclination change amount, and the position change amount, calculating the angle frequency, the inclination frequency, and the position frequency, and determining that the awakening degree of the driver of the subject vehicle decreases when at least one of the angle frequency, the inclination frequency, and the position frequency exceeds the fourth threshold value, the fifth threshold value, and the sixth threshold value. In other words, this program is also deemed to make a computer execute a procedure or a method of the change amount acquisition unit 21 etc. Herein, the memory 83 may be a non-volatile or volatile semiconductor memory such as a RAM (Random Access Memory), a ROM (Read Only Memory), a flash memory, an EPROM (Electrically Programmable Read Only Memory), or an EEPROM (Electrically Erasable Programmable Read Only Memory), an HDD (Hard Disk Drive), a magnetic disc, a flexible disc, an optical disc, a compact disc, a mini disc, a DVD (Digital Versatile Disc), or a drive device of them, or any storage medium which is to be used in the future.

Described above is the configuration that each function of the change amount acquisition unit 21 etc. is achieved by one of the hardware and the software, for example. However, the configuration is not limited thereto, but also applicable is a configuration of achieving a part of the change amount acquisition unit 21 etc. by dedicated hardware and achieving another part of them by software, for example. For example, the function of the change amount acquisition unit 21 can be achieved by a processing circuit 81 as the dedicated hardware and a receiver, for example, and the function of the other units can be achieved by the processing circuit 81 as the processor 82 reading out and executing the program stored in the memory 83.

As described above, the processing circuit 81 can achieve each function described above by the hardware, the software, or the combination of them, for example.

The awakening degree determination apparatus described above can also be applied to a navigation device such as a Portable Navigation Device (PND), a communication terminal including a portable terminal such as a mobile phone, a smartphone, or a tablet, for example, a function of an application installed on at least one of the navigation device and the communication terminal, and an awakening degree determination system constructed as a system by appropriately combining a server, for example. In this case, each function or each constituent element of the awakening degree determination apparatus described above may be dispersedly disposed in each apparatus constructing the system, or may also be collectively disposed in one of the apparatuses. For example, the awakening degree determination apparatus may further include at least one of the steering angle detection unit 110, the inclination detection unit 120, the lateral position detection unit 130, and the output unit 310 illustrated in FIG. 2. For example, also applicable is a configuration that the server includes a navigation function and the navigation device includes only a display function and a position detection function.

Figure 28:
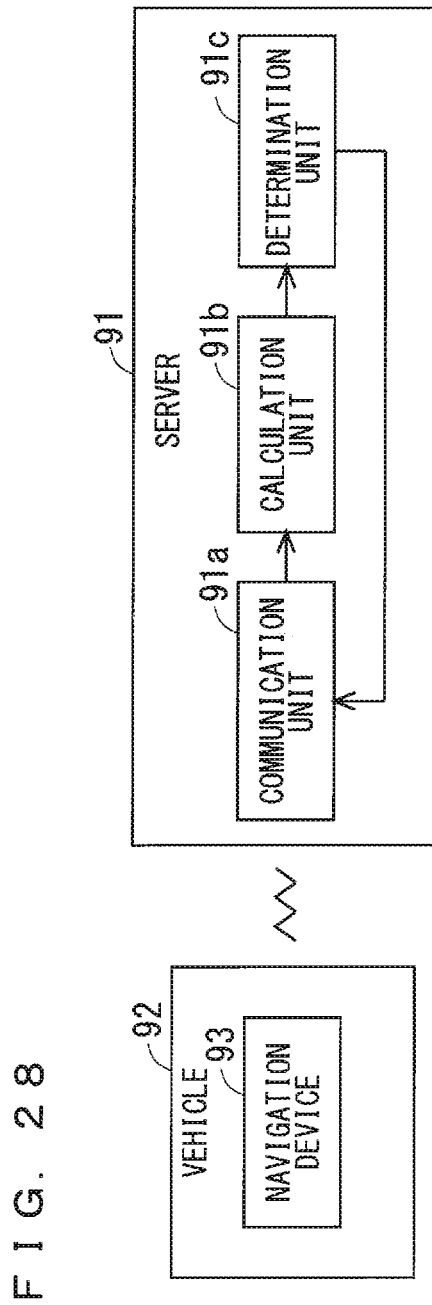
FIG. 28 A block diagram illustrating a configuration of a server according to a modification example.

FIG. 28 is a block diagram illustrating a configuration of a server 91 according to a present modification example. The server 91 illustrated in FIG. 28 includes a communication unit 91a, a calculation unit 91b, and a determination unit 91c, and can perform a wireless communication with a navigation device 93 in a vehicle 92.

The communication unit 91a which is the change amount acquisition unit performs the wireless communication with the navigation device 93, thereby receiving the angle change amount, the inclination change amount, and the position change amount acquired in the navigation device 93. The calculation unit 91b calculates the angle frequency, the inclination frequency, and the position frequency based on the angle change amount, the inclination change amount, and the position change amount received in the communication unit 91a. When at least one of the angle frequency, the inclination frequency, and the position frequency calculated in the calculation unit 91b exceeds the fourth threshold value, the fifth threshold value, and the sixth threshold value, the determination unit 91c determines that the awakening degree of the driver of the subject vehicle decreases. Then, the communication unit 91a transmits a determination result of the determination unit 91c to the navigation device 93. According to the server 91 having such a configuration, the effect similar to that of the awakening degree determination apparatus described in the embodiment 1 can be acquired.

FIG. 29 is a block diagram illustrating a configuration of a communication terminal 96 according to a present modification example. The communication terminal 96 illustrated in FIG. 29 includes a communication unit 96a similar to the communication unit 91a, a calculation unit 96b similar to the calculation unit 91b, and a determination unit 96c similar to the determination unit 91c, and can performs a wireless communication with a navigation device 98 in a vehicle 97. A mobile terminal such as a mobile phone, a smartphone, and a tablet carried by a driver of the vehicle 97, for example, is applied to the communication terminal 96. According to the communication terminal 96 having such a configuration, the effect similar to that of the awakening degree determination apparatus described in the embodiment 1 can be acquired.

According to the present invention, each embodiment can be arbitrarily combined, or each embodiment can be appropriately varied or omitted within the scope of the invention.

Although the present invention is described in detail, the foregoing description is in all aspects illustrative and does not restrict the invention. It is therefore understood that numerous modifications and variations can be devised without departing from the scope of the invention.

EXPLANATION OF REFERENCE SIGNS 21 change amount acquisition unit, 22 frequency calculation unit, 23 awakening degree determination unit

The invention claimed is:

1. An awake degree determination apparatus, comprising:
a processor to execute a program; and
a memory to store the program which, when executed by the processor, performs
a change amount acquisition process acquiring an angle change amount which is a change amount of a steering angle of a vehicle in a first period which is predetermined, an inclination change amount which is a change amount of an inclination of a front and rear side of the vehicle with respect to a travel traffic lane of the vehicle in a second period which is predetermined, and a position change amount which is a change amount of a lateral position of the vehicle in the travel traffic lane in a third period which is predetermined;
a frequency calculation process calculating an angle frequency which is a frequency in which the angle change amount exceeds a first threshold value which is predetermined, an inclination frequency which is a frequency in which the inclination change amount exceeds a second threshold value which is predetermined, and a position frequency which is a frequency in which the position change amount exceeds a third threshold value which is predetermined; and
an awake degree determination process determining that an awake degree of a driver of the vehicle decreases when at least one of the angle frequency, the inclination frequency, and the position frequency exceeds a fourth threshold value, a fifth threshold value, and a sixth threshold value which are predetermined on the angle frequency, the inclination frequency, and the position frequency, respectively wherein
the awake degree determination process determines that the awake degree decreases when the change amount acquisition process cannot acquire the inclination change amount or the position change amount and the angle frequency exceeds the fourth threshold value.

2. The awake degree determination apparatus according to claim 1, wherein
the angle change amount is a difference between a maximum value and a minimum value of the steering angle in the first period,
the inclination change amount is a difference between a maximum value and a minimum value of the inclination in the second period, and
the position change amount is a difference between a maximum value and a minimum value of the lateral position in the third period.

3. The awake degree determination apparatus according to claim 1, wherein
the angle change amount, the inclination change amount, and the position change amount are calculated only when a curvature change of the travel traffic lane in a predetermined period is equal to or smaller than a predetermined threshold value.

4. The awake degree determination apparatus according to claim 1, wherein
the angle change amount, the inclination change amount, and the position change amount are calculated only when a direction indicator of the vehicle is in an off-state.

5. The awake degree determination apparatus according to claim 1, wherein
the first threshold value, the second threshold value, and the third threshold value are determined based on individual information on a drive technique or a drive property of the driver.

6. The awake degree determination apparatus according to claim 1,
wherein the first period is a duration time of the corrected steering in the vehicle, the second period is a time based on a cycle in which the inclination takes an extreme value, and the third period is a time based on a meandering of the vehicle.

7. The awake degree determination apparatus according to claim 1,
wherein a length of the third period is different from each of a length of the first period and a length of the second period.

8. An awake degree determination method, comprising:
acquiring an angle change amount which is a change amount of a steering angle of a vehicle in a first period which is predetermined, an inclination change amount which is a change amount of an inclination of a front and rear side of the vehicle with respect to a travel traffic lane of the vehicle in a second period which is predetermined, and a position change amount which is a change amount of a lateral position of the vehicle in the travel traffic lane in a third period which is predetermined;
calculating an angle frequency which is a frequency in which the angle change amount exceeds a first threshold value which is predetermined, an inclination frequency which is a frequency in which the inclination change amount exceeds a second threshold value which is predetermined, and a position frequency which is a frequency in which the position change amount exceeds a third threshold value which is predetermined;
determining that an awake degree of a driver of the vehicle decreases when at least one of the angle frequency, the inclination frequency, and the position frequency exceeds a fourth threshold value, a fifth threshold value, and a sixth threshold value which are predetermined on the angle frequency, the inclination frequency, and the position frequency, respectively; and
determining that the awake degree decreases when the inclination change amount or the position change amount cannot be acquired and the angle frequency exceeds the fourth threshold value.

9. An awake degree determination apparatus, comprising:
a processor to execute a program; and
a memory to store the program which; when executed by the processor, performs a change amount acquisition process acquiring an angle change amount which is a change amount of a steering angle of a vehicle in a first period which is predetermined, an inclination change amount which is a change amount of an inclination of a front and rear side of the vehicle with respect to a travel traffic lane of the vehicle in a second period which is predetermined, and a position change amount which is a change amount of a lateral position of the vehicle in the travel traffic lane in a third period which is predetermined;

a frequency calculation process calculating an angle frequency which is a frequency in which the angle change amount exceeds a first threshold value which is predetermined, an inclination frequency which is a frequency in which the inclination change amount exceeds a second threshold value which is predetermined, and a position frequency which is a frequency in which the position change amount exceeds a third threshold value which is predetermined; and an awake degree determination process determining that an awake degree of a driver of the vehicle decreases when at least one of the angle frequency, the inclination frequency, and the position frequency exceeds a fourth threshold value, a fifth threshold value, and a sixth threshold value which are predetermined on the angle frequency, the inclination frequency; and the position frequency, respectively, wherein the first threshold value, the second threshold value, and the third threshold value are determined based on individual information on a drive technique or a drive property of the driver and a regression expression obtained from the individual information of a plurality of drivers which include the driver.

10. The awake degree determination apparatus according to claim 9, wherein the individual information includes the angle change amount in the first period in a predetermined fourth period after a driving of the vehicle is started, the inclination change amount in the second period in the fourth period, and the position change amount in the third period in the fourth period.

* * * * *